US008246987B2

(12) United States Patent
Yamamoto et al.

(10) Patent No.: US 8,246,987 B2
(45) Date of Patent: Aug. 21, 2012

(54) CONTROLLED RELEASE COMPOSITION AND METHOD OF PRODUCING THE SAME

(75) Inventors: Kazumichi Yamamoto, Kyoto (JP); Akiko Yamada, Kyoto (JP); Yoshio Hata, Hokkaido (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/064,282

(22) Filed: Mar. 16, 2011

(65) Prior Publication Data

US 2011/0166084 A1    Jul. 7, 2011

Related U.S. Application Data

(60) Division of application No. 12/181,472, filed on Jul. 29, 2008, which is a continuation of application No. 10/182,731, filed as application No. PCT/JP02/06527 on Jun. 28, 2002, now Pat. No. 7,429,559.

(30) Foreign Application Priority Data

Jun. 29, 2001 (JP) .................. 2001-199484
Nov. 6, 2001 (JP) .................. 2001-340993

(51) Int. Cl.
*A61K 38/08* (2006.01)
(52) U.S. Cl. .................. 424/468; 514/21.6; 514/784
(58) Field of Classification Search .................. None
See application file for complete search history.

(56) References Cited

U.S. PATENT DOCUMENTS

| 3,297,033 | A | 1/1967 | Schmitt et al. |
|---|---|---|---|
| 3,565,869 | A | 2/1971 | DeProspero |
| 3,755,558 | A | 8/1973 | Scribner |
| 3,773,919 | A | 11/1973 | Boswell et al. |
| 3,839,297 | A | 10/1974 | Wasserman et al. |
| 3,890,283 | A | 6/1975 | Casey et al. |
| 3,912,692 | A | 10/1975 | Casey et al. |
| 4,249,531 | A | 2/1981 | Heller et al. |
| 4,258,063 | A | 3/1981 | Chun et al. |
| 4,273,920 | A | 6/1981 | Nevin |
| 4,479,911 | A | 10/1984 | Fong |
| 4,539,981 | A | 9/1985 | Tunc |
| 4,605,730 | A | 8/1986 | Shalaby et al. |
| 4,652,441 | A | 3/1987 | Okada et al. |
| 4,677,191 | A | 6/1987 | Tanaka et al. |
| 4,728,721 | A | 3/1988 | Yamamoto et al. |
| 4,767,628 | A | 8/1988 | Hutchinson |
| 4,801,739 | A | 1/1989 | Franz et al. |
| 4,849,228 | A | 7/1989 | Yamamoto et al. |
| 5,594,091 | A | 1/1997 | Igari et al. |
| 5,665,394 | A | 9/1997 | Igari et al. |
| 5,763,513 | A | 6/1998 | Suzuki et al. |
| 5,922,682 | A | 7/1999 | Brich et al. |
| 6,113,943 | A | 9/2000 | Okada et al. |
| 6,353,086 | B1 | 3/2002 | Kolstad et al. |
| 6,565,874 | B1 | 5/2003 | Dunn et al. |
| 6,699,500 | B2 | 3/2004 | Okada et al. |
| 6,740,634 | B1 * | 5/2004 | Saikawa et al. .............. 514/10.1 |
| 7,265,157 | B1 * | 9/2007 | Igari et al. ................. 514/772.1 |

FOREIGN PATENT DOCUMENTS

| CA | 2 316 273 | A1 | 7/1999 |
|---|---|---|---|
| EP | 0 145 240 | A2 | 6/1985 |
| EP | 0 190 833 | | 8/1986 |
| EP | 0 202 065 | B1 | 4/1993 |
| EP | 0 586 238 | A2 | 3/1994 |
| EP | 0 052 510 | B2 | 10/1994 |
| EP | 0 668 073 | A2 | 8/1995 |
| EP | 0 839 525 | A1 | 5/1998 |
| EP | 1 048 301 | A1 | 11/2000 |
| EP | 1 158 014 | A1 | 11/2001 |
| EP | 1 197 208 | A1 | 4/2002 |
| EP | 0 058 481 | B2 | 5/2003 |
| EP | 1 310 517 | A1 | 5/2003 |
| EP | 1 310 517 | B1 | 4/2006 |
| GB | 2 145 422 | A | 3/1985 |
| JP | 6-78425 | B2 | 10/1994 |
| JP | 7-278277 | A | 10/1995 |
| JP | 8-259460 | A | 10/1996 |
| JP | 9-132524 | A | 5/1997 |
| JP | 10-273447 | A | 10/1998 |

(Continued)

OTHER PUBLICATIONS

Beck et al., "Systemic and local delivery of contraceptive steroids using biodegradable microcapsules," Progress in Contraceptive Delivery Systems, 1980, vol. 1, 63-81.
Bittner et al., "Bovine serum albumin loaded poly(lactide-co-glycolide) microspheres: the influence of polymer purity on particle characteristics," J. Microencapsulation, 1998, 15(4):495-514.
Braun et al., Praktical Macromolecular Organic Chemistry, 1966, any edition, 57-59 (English translation attached).
Brock, Thomas D., "Membrane Filtration, A User's Guide and Reference Manual," Science Tech, Inc., 1983, 290-291.
Collins et al., "Isolation and Purification of Polymer," Experiments in Polymer Science, 1973, pp. 62-69.
Eisenbach, Prof. Dr. Claus D., Expert Opinion of Apr. 4, 2006 in EP 1 310 517, 44 pages.

(Continued)

*Primary Examiner* — Christopher R. Tate
*Assistant Examiner* — Roy Teller
(74) *Attorney, Agent, or Firm* — Foley & Lardner LLP

(57) ABSTRACT

A controlled release composition containing a physiologically active substance in high content, suppressing the initial excess release, and achieving a stable release speed over a long period of time is provided.
A controlled release composition comprising (1) a physiologically active substance or salt thereof in an amount of about 14% (w/w) to about 24% (w/w) based on the total composition weight, (2) hydroxynaphthoic acid selected from the group consisting of 3-hydroxy-2-naphthoic acid and 1-hydroxy-2-naphthoic acid or salt thereof, and (3) a lactic acid polymer or salt thereof having a weight-average molecular weight of 15000 to 50000 in which the content of polymers having molecular weights of 5000 or less is about 5% by weight or less, wherein the molar ratio of said hydroxynaphthoic acid or salt thereof to said physiologically active substance or salt thereof is from 3:4 to 4:3.

9 Claims, No Drawings

FOREIGN PATENT DOCUMENTS

| | | |
|---|---|---|
| JP | 11-269094 A | 10/1999 |
| JP | 2001-081043 A | 3/2001 |
| WO | WO 95/15767 A1 | 6/1995 |
| WO | WO 00/35990 A1 | 6/2000 |
| WO | WO 01/05380 A1 | 1/2001 |
| WO | WO 02/12369 A1 | 2/2002 |
| WO | WO 02/43766 A1 | 6/2002 |
| WO | WO 02/47722 A1 | 6/2002 |

OTHER PUBLICATIONS

Encyclopedic Handbook of Biomaterials and Bioengineering, Part A: Materials, vol. 2, 1995, 1014-1054.

Final Notification of Reasons for Rejection dated Sep. 15, 2009, in corresponding JP 2004-117981, 3 pages, with English translation, 2 pages.

Kulkarni et al., "Biodegradable Poly(lactic acid) Polymers," J. Biomed. Mater. Res., 1971, 5, 169-181.

Miller et al., "Degradation Rates of Oral Resorbable Implants (Polylactates and Polyglycolates): Rate Modification with Changes in PLA/PGA Copolymer Ratios," J. Biomed. Mater. Res., 1977, 11, 711-719.

Nagata et al., " Pharmaceutical Dosage Form Design of Copoly (Lactic/Glycolic Acid) Microspheres, Mechanism of in Vitro Release of Gentamicin," Yakugaku Zasshi, 1994, 114(12):1005-1014, with English abstract.

Office Action issued Dec. 19, 2008, in counterpart Chinese Application No. 200610093268.X, 5 pages.

Office Action mailed Jun. 16, 2009, in corresponding Japanese Application No. 2004-117981, 3 pages, with English translation, 3 pages.

Pitt et al., "Sustained Drug Delivery Systems. I. The Permeability of Poly(ϵ-Caprolactone), Poly(DL-Lactic Acid), and Their Copolymers," J. Biomed. Mater. Res., 1979, 13, 497-507.

Psychrembel Klinisches Wörterbuch, 1994, 257, Ed., de Gruyter Ed., sections "BnRH" and "GnRH-Agonisten," 3 pages.

Rompp Chemie Lexikon, Falbe et al., Ed., 1991 Georg Thieme Verlag, 3107-3108, and English translation (4 pgs.).

Rote Liste, 2000, section 50 036 "Enantone," section 50 038 "Kryptocur," and section 50 039 "Lutrelef," 3 pages.

Ruiz et al., "Influence of Average Molecular Weights of Poly(DL-Lactic Acid-Co-Glycolic Acid) Copolymers 50/50 on Phase Separation and in Vitro Drug Release from Microspheres," Pharmaceutical Research, 1990, 7(9):928-934.

Schartel et al., "Dielectric and thermodynamic properties of biodegradable poly(D,L-lactide-co-glycolide) and the effect of the microencapsulation and release of captopril," J. Microencapsulation, 1997, 14(4):475-488.

Schindler et al., "Biodegradable polymers for sustained drug delivery," Contemporary Topics in Polymer Science, Eli M. Pearce et al., Ed., 1977, 2, pp. 251-289.

Sezaki, Hitoshi, Drug Delivery System, 1986, 186-189.

Suzuki et al., "Microencapsulation and Dissolution Properties of a Neuroleptic in a Biodegradable Polymer, Poly(d,l-lactide)," J. Pharm. Science, Jan. 1985, 74(1), 21-25.

Taguchi et al., "Long-term clinical study on TAP-144-SR, an LH-RH agonist depot formulation, in premenopausal patients with advanced or recurrent breast cancer. TAP-144-SR Breast Cancer Study Group," Gan to Kagaku Ryoho, Mar. 1995, 22(4):495-508, with PubMed English Abstract, 15 pages.

The Merck Index, 1989, $11^{th}$ Ed., entry 4433 "Goserelin," p. 711, 3 pages.

The Merck Index, 1989, $11^{th}$ Ed., entry 9662 "Triptorelin," pp. 1533-1534, 4 pages.

The Merck Index, 2001, $13^{th}$ Ed., entry 5478, "Leuprolide," 3 pages.

Tracy et al., "Factors affecting the degradation rate of poly(lactic-co-glycolide) microspheres in vivo and in vitro," Biomaterials, 1999, 20:1057-1062.

Vert et al., "Bioresorbable Plastic Materials for Bone Surgery," Macromolecular Biomaterials, 1984, Chapter 6, 119-142.

Vert et al., "Stereoregular Bioresorbable Polyesters for Orthopedic Surgery," Makromol. Chem. Suppl., 1981, 5, 30-41.

Woo et al., "In Vitro Characterization and in Vivo Testosterone Suppression of 6-Month Release Poly(D,L-Lactide) Leuprolide Microspheres," Pharmaceutical Research (Apr. 2002), vol. 19, No. 4, pp. 546-550, Plenum Publishing Corporation.

Woodland et al., "Long-Acting Delivery Systems for Narcotic Antagonists," J. Med. Chem., 1973, 16(8), 897-901.

Zhou et al., "Clinical Use of Gonadotropin-Releasing Hormone Agonist," China Practical Gynecology and Obstetrics Magazine, Dec. 1999, 15(12):754-756, with English translation.

Expert Opinion of Prof. Dr. Claus D. Eisenbach (II, Exhibit No. 3) with Exhibits and Appendix, signed Dec. 6, 2006, cited during Opposition Proceedings of corresponding European Patent No. 1330293, 18 pages.

Expert Opinion of Prof. Dr. Claus D. Eisenbach (III, Exhibit No. 4) with Exhibits and Appendices, signed Dec. 6, 2006, cited during Opposition Proceedings of corresponding European Patent No. 1330293, 18 pages.

English translation of WO 00/35990 (cited in IDS filed Mar. 16, 2011), 66 pages.

Affidavit of Richard L. Norton Ph.D., signed Aug. 15, 2008, cited during Opposition Proceedings of corresponding European Patent No. 1330293, 14 pages.

Affidavit of Mark E. Medina Ph.D., signed Sep. 18, 2008, cited during Opposition Proceedings of corresponding European Patent No. 1330293, 43 pages.

* cited by examiner

CONTROLLED RELEASE COMPOSITION AND METHOD OF PRODUCING THE SAME

CROSS-REFERENCE TO RELATED APPLICATIONS

This application is a Divisional of U.S. application Ser. No. 12/181,472, filed Jul. 29, 2008, which is a Continuation of U.S. application Ser. No. 10/182,731, which is the U.S. National Stage application of PCT/JP02/06527, filed Jun. 28, 2002, now U.S. Pat. No. 7,429,559, which claims priority from Japanese patent applications JP 2001-199484, filed Jun. 29, 2001, and JP 2001-340993, filed Nov. 6, 2001.

TECHNICAL FIELD

The present invention relates to a controlled release composition of a physiologically active substance, a method of producing the same, and a use as a medicine and the like.

BACKGROUND ART

Biodegradable polymers having controlled releasing property are useful, for example, as base materials of microcapsules and the like for containing a physiologically active substance. It is known that, as such biodegradable polymers, polymers containing polylactic acid, a copolymer of lactic acid and glycolic acid, and the like are useful (JP-A No. 11-269094 and the like).

As these biodegradable polymers, those produced by a conventional synthesis method have been used themselves, however, it has been found that those produced themselves have poor availability as a controlled release base material since they have low content of end carboxyl groups. Therefore, it has been studied to hydrolyze an biodegradable polymer as described above having higher molecular weight to control the weight-average molecular weight thereof to suitable level, before use as a base material for a controlled release preparation.

However, polymers obtained by hydrolysis and water-washing tend to cause an initial burst of physiologically active substance, rendering them unsuitable as a controlled release base material, even if they have an appropriate weight-average molecular weight and end carboxyl group content. Therefore, an improvement is desired in current conditions.

JP-A No. 7-97334 discloses a controlled release preparation composed of a physiologically active peptide or salt thereof and an biodegradable polymer having a free carboxyl group at the end, and a method of producing the same.

GB2209937, GB2234169, GB2234896, GB2257909 and EP626170A2 disclose a composition containing as a base material a biodegradable polymer containing a water-insoluble salt such as pamoates of peptide and protein prepared separately, and a method of producing this composition.

WO95/15767 discloses an embonate (pamoate) of cetrorelix (LH-RH-antagonist) and a method of producing the same, and simultaneously describes that even if this pamoate is enclosed in an biodegradable polymer, the peptide releasing property thereof is the same as for a pamoate alone.

OBJECTS OF THE INVENTION

An object of the present invention is to provide a novel composition containing a physiologically active substance in high content and capable of achieving a stable releasing speed for a long period of time by suppressing the initial excess release of pharmaceutically active substance, and a method of producing the same.

SUMMARY OF THE INVENTION

The present inventors have intensively investigated in view of the above-mentioned conditions, and ultimately succeeded in producing a lactic acid polymer or salt thereof not readily causing the initial excess release, by reducing the content of a lactic acid polymer of lower molecular weight, particularly, that having a weight-average molecular weight of 5000 or less in an biodegradable polymer, and found that a controlled release preparation containing this lactic acid polymer or salt thereof can incorporate a physiologically active substance in unexpectedly high content and that a stable releasing speed for a long period of time can be achieved by suppressing the initial excess release.

Further, the present inventors have found that if a physiologically active substance is incorporated in high content in a composition by allowing a physiologically active substance and hydroxynaphthoic acid to coexist in forming the composition and further both of them are enclosed in a lactic acid polymer or salt thereof, then, the physiologically active substance is released at a different speed from the releasing speed of a physiologically active substance from a composition formed of a physiologically active substance and hydroxynaphthoic acid prepared in the absence of a lactic acid polymer or salt thereof, and the releasing speed can be controlled by the property of the biodegradable polymer and the addition amount of hydroxynaphthoic acid, and even at high content, the initial excess release can be suppressed effectively and sustained release for a very long period of time can be achieved.

The present inventors have further studied based on this knowledge, and completed the present invention as a result.

Namely, the present invention provides (1). A controlled release composition comprising (1) a physiologically active substance or salt thereof in an amount of about 14% (w/w) to about 24% (w/w) based on the total composition weight, (2) hydroxynaphthoic acid selected from the group consisting of 3-hydroxy-2-naphthoic acid and 1-hydroxy-2-naphthoic acid or salt thereof, and (3) a lactic acid polymer or salt thereof having a weight-average molecular weight of 15000 to 50000 in which the content of polymers having molecular weights of 5000 or less is about 5% by weight or less, wherein the molar ratio of the hydroxynaphthoic acid or salt thereof to the physiologically active substance or salt thereof is from 3:4 to 4:3, (2). The controlled release composition according to (1) wherein the lactic acid polymer has a weight-average molecular weight of 15000 to 30000, (3). The controlled release composition according to (1) wherein the physiologically active substance is a LH-RH derivative, (4). The controlled release composition according to (3) wherein the LH-RH derivative is a peptide of the formula:

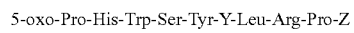
5-oxo-Pro-His-Trp-Ser-Tyr-Y-Leu-Arg-Pro-Z

[wherein, Y represents DLeu, DAla, DTrp, DSer(tBu), D2Nal or DHis(ImBzl), and Z represents $NH-C_2H_5$ or $Gly-NH_2$.], or a salt thereof, (5). The controlled release composition according to (1) wherein the physiologically active substance or salt thereof is a LH-RH derivative of the formula:

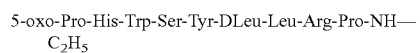
5-oxo-Pro-His-Trp-Ser-Tyr-DLeu-Leu-Arg-Pro-NH—
$C_2H_5$ or an acetate salt thereof, and the hydroxynaphthoic acid is 3-hydroxy-2-naphthoic acid or 1-hydroxy-2-naphthoic acid, (6). A medicine comprising the controlled release composition according to (1), (7). A preventive or curative drug for prostatic cancer, prostatic hyperplasia, endometriosis, uterine myoma, uterine fibroma, precocious puberty, dysmenorrhea or breast cancer or a contraceptive agent, comprising the controlled release composition according to (3), (8). An agent for preventing recurrence of breast cancer after the operation for premenopausal breast cancer, which comprises the sustained-release composition according to (3).

(9). A method of preventing or curing prostatic cancer, prostatic hyperplasia, endometriosis, uterine myoma, uterine fibroma, precocious puberty, dysmenorrhea or breast cancer or a method of contraception, comprising administrating an effective amount of the controlled release composition according to (3) to mammals, (10). A method for preventing recurrence of breast cancer after the operation for premenopausal breast cancer, which comprises administering to a mammal an effective dose of the sustained-release composition according to (3).

(11). A controlled release composition comprising a physiologically active substance or salt thereof, and a lactic acid polymer or salt thereof having a weight-average molecular weight of 15000 to 50000 in which the content of polymers having molecular weights of 5000 or less is about 5% by weight or less, (12). A controlled release composition comprising a physiologically active substance or salt thereof, hydroxynaphthoic acid or salt thereof, and a lactic acid polymer or salt thereof having a weight-average molecular weight of 15000 to 50000 in which the content of polymers having molecular weights of 5000 or less is about 5% by weight or less, (13). The controlled release composition according to (11), comprising (1) a physiologically active substance or salt thereof in an amount of about 3% (w/w) to about 24% (w/w) based on the total composition weight, and (2) a lactic acid polymer or salt thereof having a weight-average molecular weight of 15000 to 50000 in which the content of polymers having molecular weights of 5000 or less is about 5% by weight or less, (14). The controlled release composition according to any of (11) to (13) wherein the lactic acid polymer has a content of polymers having molecular weights of 3000 or less is about 1.5% by weight or less, (15). The controlled release composition according to any of (11) to (13) wherein the lactic acid polymer has a content of polymers having molecular weights of 1000 or less is about 0.1% by weight or less, (16). The controlled release composition according to any of (11) to (15) wherein the lactic acid polymer has a weight-average molecular weight of 15000 to 40000, (17). The controlled release composition according to any of (11) to (15) wherein the lactic acid polymer has a weight-average molecular weight of 17000 to 26000, (18). The controlled release composition according to (12) wherein the hydroxynaphthoic acid is 3-hydroxy-2-naphthoic acid or 1-hydroxy-2-naphthoic acid, (19). The controlled release composition according to (11) or (13) wherein the physiologically active substance is a physiologically active peptide, (20). The controlled release composition according to (12) wherein the physiologically active substance is a physiologically active peptide, (21). The controlled release composition according to (19) wherein the physiologically active substance is a LH-RH derivative, (22). The controlled release composition according to (20) wherein the physiologically active substance is a LH-RH derivative, (23). The controlled release composition according to (21) or (22) wherein the LH-RH derivative is a peptide of the formula:

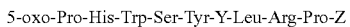

5-oxo-Pro-His-Trp-Ser-Tyr-Y-Leu-Arg-Pro-Z

[wherein, Y represents DLeu, DAla, DTrp, DSer(tBu), D2Nal or DHis(ImBzl), and Z represents NH—$C_2H_5$ or Gly-$NH_2$.], or a salt thereof, (24). The controlled release composition according to (21) wherein the LH-RH derivative or salt thereof is contained in an amount of 3% (w/w) to 24% (w/w) in the controlled release composition, (25). The controlled release composition according to (22) wherein the molar ratio of the hydroxynaphthoic acid or salt thereof to the LH-RH derivative or salt thereof is from 3:4 to 4:3, (26). The controlled release composition according to (22) wherein the LH-RH derivative or salt thereof is contained in an amount of 14% (w/w) to 24% (w/w) in the controlled release composition, (27). The controlled release composition according to any of (11) to (13) which is used for injection, (28). A method of producing the controlled release composition according to (11), comprising removing a solvent from a mixed solution of a physiologically active substance or salt thereof, and a lactic acid polymer or salt thereof having a weight-average molecular weight of 15000 to 50000 in which the content of polymers having molecular weights of 5000 or less is about 5% by weight or less, (29). A method of producing the controlled release composition according to (12), comprising removing a solvent from a mixed solution of a physiologically active substance or salt thereof, hydroxynaphthoic acid or salt thereof, and a lactic acid polymer or salt thereof having a weight-average molecular weight of 15000 to 50000 in which the content of polymers having molecular weights of 5000 or less is about 5% by weight or less, (30). The method of producing a controlled release composition according to (29), comprising mixing and dispersing a physiologically active substance or salt thereof into an organic solvent solution containing hydroxynaphthoic acid or salt thereof, and a lactic acid polymer or salt thereof having a weight-average molecular weight of 15000 to 50000 in which the content of polymers having molecular weights of 5000 or less is about 5% by weight or less, then, removing said organic solvent, (31). The method of producing a controlled release composition according to (30) wherein the physiologically active substance or salt thereof is an aqueous solution containing a physiologically active substance or salt thereof, (32). The production method according to (30) wherein the salt of a physiologically active substance is a salt with a free base or acid, (33). A medicine comprising the controlled release composition according to any of (11) to (13), (34). A preventive or curative drug for prostatic cancer, prostatic hyperplasia, endometriosis, uterine myoma, uterine fibroma, precocious puberty, dysmenorrhea or breast cancer or a contraceptive agent, comprising the controlled release composition according to (21) or (22),

(35) An agent for preventing recurrence of breast cancer after the operation for premenopausal breast cancer, comprising the controlled release composition according to (21) or (22), (36). A method of preventing or curing prostatic cancer, prostatic hyperplasia, endometriosis, uterine myoma, uterine fibroma, precocious puberty, dysmenorrhea or breast cancer or a method of contraception, comprising administrating an effective amount of the controlled release composition according to (21) or (22), to mammals, and (37). A method of preventing recurrence of breast cancer after the operation for premenopausal breast cancer, comprising administrating an effective amount of the controlled release composition for mammals according to (21) or (22), to mammals.

Further, the present invention provides

(38) The controlled release composition according to (12) wherein the amount of hydroxynaphthoic acid or salt thereof compounded is about 1 to about 7 mol, preferably about 1 to about 2 mol based on 1 mol of a physiologically active peptide or salt thereof,

(39) The method of producing the controlled release composition according to (29) comprising producing a W/O type emulsion in which liquid containing a physiologically active substance or salt thereof is an inner aqueous phase and a solution containing a lactic acid polymer or salt thereof and hydroxynaphthoic acid or salt thereof is an oil phase, then, removing a solvent,

(40) The method of producing the controlled release composition according to (29) comprising producing a W/O type emulsion in which liquid containing hydroxynaphthoic acid or salt thereof is an inner aqueous phase and a solution containing a physiologically active substance or salt thereof and a lactic acid polymer or salt thereof is an oil phase, then, removing a solvent, and

(41) The method of producing the controlled release composition according to (39) or (40) wherein the method of removing a solvent is an in-water drying method, and the like.

DETAILED DESCRIPTION OF THE INVENTION

The physiologically active substance used in the present invention is not particularly restricted providing it is pharmaceutically useful, and may be a non-peptide compound or a peptide compound. As the non-peptide compound, agonists, antagonists, compounds having an enzyme inhibition action, and the like are listed. As the peptide compound, for example, physiologically active peptides are preferable, and physiologically active peptides having molecular weights of about 300 to about 40000, preferably about 400 to about 30000, further preferably about 500 to about 20000, and the like are suitable.

As the physiologically active peptide, there are mentioned, for example, luteinizing hormone releasing hormone (LH-RH), insulin, somatostatin, growth hormone, growth hormone releasing hormone (GH-RH), prolactin, erythropoietin, adenocorticotropic hormone, melanocyte stimulating hormone, thyroid hormone releasing hormone, thyroid stimulating hormone, luteinizing hormone, follicle stimulating hormone, vasopressin, oxytocin, calcitonin, gastrin, secretin, pancreozymin, cholecystokinin, angiotensin, human placental lactogen, human chorionic gonadotropin, enkephalin, endorphin, Kyotorphin, tuftsin, thymopoietin, thymosin thymozymrin, thymus humoral factor, blood thymus factor, tumor necrosis factor, colony inducer, motilin, dynorphin, bombesin, neurotensin, cerulein, bradykinin, atrial natriuretic factor, nerve growth factor, cell growth factor, nerve nutritional factor, peptides and the like having an encloserine antagonistic action, and derivatives thereof, further, fragments thereof or derivatives of fragments, and the like.

The physiologically active substance used in the present invention may be itself or a pharmaceutically acceptable salt.

As such a salt, when the above-mentioned physiologically active substance has a basic group such as an amino group, there are listed salts with inorganic acids (also called inorganic free acid) (for example, carbonic acid, bicarbonic acid, hydrochloric acid, sulfuric acid, nitric acid, boric acid and the like) and organic acids (also called organic free acid) (for example, succinic acid, acetic acid, propionic acid, trifluoroacetic acid and the like) and the like.

When the physiologically active substance has an acidic group such as a carboxyl group and the like, there are listed salts with inorganic bases (also called inorganic free base) (for example, alkali metals such as sodium, potassium and the like, alkaline earth metals such as calcium, magnesium and the like) and organic bases (also called organic free base) (for example, organic amines such as triethylamine and the like, basic amino acids such as arginine and the like) and the like. The physiologically active peptide may form a metal complex compound (for example, copper complex, zinc complex and the like).

As the preferable examples of the physiologically active peptide, there are listed LH-RH derivatives or salts thereof effective on hormone-dependent diseases, particularly, sex hormone-dependent cancers (for example, prostate cancer, uterine cancer, breast cancer, pituitary tumor and the like), sex hormone-dependent diseases such as prostatic hyperplasia, endometriosis, uterine myoma, precocious puberty, dysmenorrhea, amenorrhea, premenstrual syndrome, multilocular ovary syndrome and the like and contraception (or, when rebound effect after drug withdrawal is utilized, infertility), recurrence of breast cancer after the operation for premenopausal breast cancer. Also listed are LH-RH derivatives and salts thereof effective on benign or malignant tumors which are LH-RH sensitive though sex hormone-independent.

Specific examples of the LH-RH derivative and salt thereof include peptides described in Treatment with GnRH analogs: Controversies and perspectives [published by The Parthenon Publishing Group Ltd., 1996], Japanese Patent Application National Publication (Laid-Open) No. 3-503165, and JP-A Nos. 3-101695, 7-97334 and 8-259460, and the like.

As the LH-RH derivative, a LH-RH agonist and LH-RH antagonist are listed, and as the LH-RH antagonist, for example, physiologically active peptides of the general formula [I]

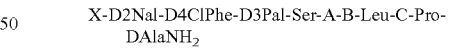

[wherein, X represents N(4H$_2$-furoyl)Gly or NAc, A represents a residue selected from NMeTyr, Tyr, Aph(Atz) and NMeAph(Atz), B represents a residue selected from DLys (Nic), DCit, DLys(AzaglyNic), DLys(AzaglyFur), DhArg (Et$_2$), DAph(Atz) and DhCi, and C represents Lys(Nisp), Arg or hArg(Et$_2$), respectively.]
or salts thereof and the like are used.

As the LH-RH agonist, for example, physiologically active peptides of the general formula [II]

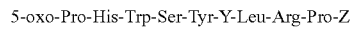

[wherein, Y represents a residue selected from DLeu, DAla, DTrp, DSer(tBu), D2Nal and DHis(ImBzl), and Z represents NH—C$_2$H$_5$ or Gly-NH$_2$, respectively.]
or salts thereof and the like are used. Particularly, a peptide in which Y represents DLeu and Z represents NH—C$_2$H$_5$ (namely, peptide A represented by 5-oxo-Pro-His-Trp-Ser-Tyr-DLeu-Leu-Arg-Pro-NH—$C_2H_5$; Leuproline) or salts thereof (for example, acetate) are suitable.

These peptide can be produced by methods described in the above-mentioned literatures or publications, or methods pursuant to them.

Abbreviations used in this specification have the following meanings.

| Abbreviation | Name |
| --- | --- |
| N(4H$_2$-furoyl)Gly: | N-tetrahydrofuroylglycine residue |
| NAc: | N-acetyl group |
| D2Nal: | D-3-(2-naphthyl)alanine residue |
| D4ClPhe: | D-3-(4-chloro)phenylalanine residue |
| D3Pal: | D-3-(3-pyridyl)alanine residue |
| NMeTyr: | N-methyltyrosine residue |
| Aph(Atz): | N-[5'-(3'-amino-1'H-1',2',4'-triazolyl)]phenylalanine residue |
| NMeAph(Atz): | N-methyl-[5'-(3'-amino-1'H-1',2',4'-triazolyl)]phenylalanine residue |
| DLys(Nic): | D-(e-N-nicotinoyl)lysine residue |
| Dcit: | D-citrulline residue |
| DLys(AzaglyNic): | D-(azaglycylnicotinoyl)lysine residue |
| DLys(AzaglyFur): | D-(azaglycylfuranyl)lysine residue |
| DhArg(Et$_2$): | D-(N,N'-diethyl)homoarginine residue |
| DAph(Atz): | D-N-[5'-(3'-amino-1'H-1',2',4'-triazolyl)]phenylalanine residue |
| DhCi: | D-homocitrulline residue |
| Lys(Nisp): | (e-N-isopropyl)lysine residue |
| hArg(Et$_2$): | (N,N'-diethyl)homoarginine residue |

When other amino acids are represented by abbreviations, they are based on abbreviations according to IUPAC-IUB Commission of Biochemical Nomenclature (European Journal of Biochemistry), vol. 138, pp. 9 to 37 (1984) and conventional abbreviations in the art, and when amino acids have optical isomers, they are in the form of L-amino acid unless otherwise stated.

The hydroxynaphthoic acid used in the present invention is prepared by bonding one hydroxyl group and one carboxyl group to different carbons in naphthalene. Therefore, 14 isomers in total are present in which the position of a hydroxyl group varies for carboxyl groups situated at 1-position and 2-position of a naphthalene ring. Any isomer among them may be used, and a mixture of them at any ratio may also be used. As described later, those having larger acid dissociation constants are preferable, or those having small pKa's (pKa=−log$_{10}$Ka, Ka represent acid dissociation constant) are preferable. Those having slight water-solubility are preferable.

Further, those soluble in alcohols (for example, ethanol, methanol and the like) are preferable. The term "soluble in alcohols" means that solubility in methanol is 10 g/L or more.

As the pKa of the above-mentioned hydroxynaphthoic acid isomer, the value of 3-hydroxy-2-naphthoic acid (pKa=2.708, Chemical Handbook, Basic II, The Chemical Society of Japan, published on Sep. 25, 1969) is only known, however, useful knowledge is obtained by comparing pKas of three kinds of isomers of hydroxybenzoic acid. Namely, pKas of m-hydroxybenzoic acid and p-hydroxybenzoic acid are 4 or more, while, pKa of o-hydroxybenzoic acid (salicylic acid) is extremely small (=2.754). Therefore, among the above-mentioned 14 isomers, 3-hydroxy-2-naphthoic acid, 1-hydroxy-2-naphthoic acid and 2-hydroxy-1-naphthoic acid in which a carboxyl group and a hydroxyl group are bonded to adjacent carbon atoms in a naphthalene ring are preferable. Further, 3-hydroxy-2-naphthoic acid in which a hydroxyl group is bonded to carbon at 3-position in naphthalene and a carboxyl group is bonded to carbon at 2-position is suitable.

The hydroxynaphthoic acid may be a salt. As the salt, for example, salts with inorganic bases (for example, alkali metals such as sodium, potassium and the like, alkaline earth metals such as calcium, magnesium and the like) and organic bases (for example, organic amines such as triethylamine and the like, basic amino acids such as arginine and the like) and the like, or salts and complex salts with transition metals (for example, zinc, iron, copper and the like) and the like, are listed.

A method of preparing a hydroxynaphthoate which is a physiologically active substance is exemplified below.

(1) A water-containing organic solvent solution of hydroxynaphthoic acid is passed through a weak basic ion exchange column to be adsorbed, and saturated. Then, excess hydroxynaphthoic acid is removed by passing through a water-containing organic solvent, then, ion exchange is conducted through a water-containing organic solvent solution of a physiologically active substance or salt thereof, and a solvent may advantageously be removed from the resulted effluent. As the organic solvent in this water-containing organic solvent, alcohols (for example, methanol, ethanol, and the like), acetonitrile, tetrahydrofuran, dimethylformamide and the like are used. As the method of removing the solvent for depositing the salt, methods known per se or pursuant methods are used. For example, a method of evaporating a solvent while controlling the degree of vacuum using a rotary evaporator and the like, and other methods, are listed.

(2) An ion exchange in a strong basic ion exchange column is previously exchanged to a hydroxide ion, and a water-containing organic solvent solution of a physiologically active substance or salt thereof is passed through this to convert the basic group into a group of hydroxide type. Hydroxynaphthoic acid of not more than the equivalent amount is added to and dissolved in the recovered effluent, then, the solution is concentrated to precipitate a salt which is washed with water if necessary and dried.

The lactic acid polymer used in the present invention (hereinafter, abbreviated as a lactic acid polymer of the present invention, in some cases) includes a polymer composed only of lactic acid or copolymers of lactic acid and other monomers (for example, glycolic acid and the like), and usually has a content of polymers having molecular weights of 5000 or less of about 5% by weight or less, preferably has a content of polymers having molecular weights of 5000 or less of about 5% by weight or less and a content of polymers having molecular weights of 3000 or less of about 1.5% by weight or less, further preferably has a content of polymers having molecular weights of 5000 or less of about 5% by weight or less, a content of polymers having molecular weights of 3000 or less of about 1.5% by weight or less and a content of polymers having molecular weights of 1000 or less of about 0.1% by weight or less.

The lactic acid polymer of the present invention has a weight-average molecular weight of usually from 15000 to 50000, preferably from 15000 to 30000, more preferably from 17000 to 26000, particularly preferably from 17500 to 25500.

Further, when hydroxynaphthoic acid is not contained in the controlled release preparation of the present invention, the lactic acid polymer of the present invention has a weight-average molecular weight of usually from 15000 to 50000, preferably from 15000 to 40000.

The lactic acid polymer of higher molecular weight which is a raw material of the lactic acid polymer of the present invention may be commercially available product or a polymer polymerized by a known method, and has a weight-average molecular weight of usually from 15000 to 500000, preferably from 30000 to 100000. As the known polymerization method, mentioned are, for example, methods in which lactic acid and if necessary glycolic acid are condensation-polymerized, for example, a method in which lactide is, if necessary together with glycolide, ring-opening-polymerized using a catalyst such as Lewis acids or metal salts such as for example diethylzinc, triethylaluminum, tin octylate and the like, a method in which lactide is ring-opening-polymerized in the further presence of a hydroxycarboxylic acid derivative of which carboxyl group is protected, in the above-mentioned method (for example, International Patent Publication WO00/35990 and the like), additionally, a method in which a catalyst is added under heat to lactide to cause ring-opening polymerization (for example, J. Med. Chem., 16, 897 (1973) and the like), for example, a method of copolymerizing lactide with glycolide, and other methods.

As the polymerization mode, bulk polymerization in which lactide and the like are melted and subjected to a polymerization reaction, and solution polymerization in which lactide and the like are dissolved in a suitable solvent and subjected to a polymerization reaction are listed, and among others, it is preferable from the standpoint of industrial production to use a polymer obtained by solution polymerization as a raw material of a lactic acid polymer of the present invention.

As the solvent dissolving lactide in solution polymerization, for example, aromatic hydrocarbons such as benzene, toluene, xylene and the like, decalin, dimethylformamide and the like, are listed.

For hydrolysis of the lactic acid polymer of higher molecular weight obtained as described above, a hydrolysis method known per se is used, for example, it is advantageous that the lactic acid polymer of higher molecular weight is dissolved in a suitable solvent, then, water and if necessary an acid are added to cause a reaction.

The solvent for dissolving the lactic acid polymer of higher molecular weight may advantageously be that capable of dissolving this polymer in an amount of 10-fold by weight or less of the lactic acid polymer, and specifically, halogenated hydrocarbons such as for example chloroform, dichloromethane and the like, aromatic hydrocarbons such as for example toluene, o-xylene, m-xylene, p-xylene and the like, cyclic ethers such as for example tetrahydrofuran and the like, acetone, N,N-dimethylformamide and the like are listed. When a solvent which can be used in hydrolysis of a lactic acid polymer of higher molecular weight is used in polymerizing a lactic acid polymer of higher molecular weight, operations of polymerization and hydrolysis can be conducted sequentially without isolating the polymerized lactic acid polymer of higher molecular weight.

The use amount of the solvent dissolving a lactic acid polymer of higher molecular weight is usually from 0.1 to 100-fold, preferably from 1 to 10-fold based on a lactic acid polymer which is a solute.

The amount of water to be added is usually from 0.001 to 1-fold by weight, preferably from 0.01 to 0.1-fold by weight based on a lactic acid polymer of higher molecular weight.

As the acid added if necessary, for example, inorganic acids such as for example hydrochloric acid, sulfuric acid, nitric acid and the like, organic acids such as for example lactic acid, acetic acid, trifluoroacetic acid and the like are listed, and lactic acid is preferably listed.

The amount of an acid to be added is usually from 0 to 10-fold by weight, preferably from 0.1 to 1-fold by weight based on a lactic acid polymer of higher molecular weight.

The reaction temperature for hydrolysis is usually from 0 to 150° C., preferably from 20 to 80° C.

The reaction time of hydrolysis differs depending also on the weight-average molecular weight of a lactic acid polymer of higher molecular weight and the reaction temperature, and usually from 10 minutes to 100 hours, preferably from 1 to 20 hours.

The termination period of hydrolysis treatment is judged based on the weight-average molecular weight of a hydrolyzed product. Namely, sampling is appropriately effected in hydrolysis treatment, the weight-average molecular weight of the hydrolyzed produced in the sample is measured by gel permeation chromatography (GPC), and hydrolysis treatment is stopped if the molecular weigh is confirmed to be about 15000 to 50000, preferably about 15000 to 30000, more preferably about 17000 to 26000, particularly preferably 17500 to 25500.

As the method of precipitating the intended lactic acid polymer contained, from a solution containing a hydrolyzed product obtained by subjecting a lactic acid polymer of higher molecular weight to a hydrolysis operation as described above, a method in which this hydrolyzed product-containing solution is allowed to contact with a solvent capable of precipitating the intended lactic acid polymer contained therein, and other methods are listed.

As the preferable embodiment of the hydrolyzed product-containing solution, mentioned are those obtained by dissolving about 10 to 50 wt % of a lactic acid polymer having a weight-average molecular weight of 15000 to 50000, preferably of 15000 to 30000, more preferably of 17000 to 26000, particularly preferably of 17500 to 25500 into a solvent capable of dissolving a lactic acid polymer of higher molecular weight, such as a halogenated hydrocarbon group such as for example chloroform, dichloromethane and the like, an aromatic hydrocarbon group such as for example toluene, o-xylene, m-xylene, p-xylene and the like, a cyclic ether such as for example tetrahydrofuran and the like, acetone, N,N-dimethylformamide, dichloromethane, xylene and the like. When hydroxynaphthoic acid is not contained in the controlled release composition of the present invention, those containing about 10 to 50 wt % of lactic acid polymers dissolved having weight-average molecular weights of 15000 to 50000, preferably of 15000 to 40000 are listed.

As the solvent which can deposit the intended lactic acid polymer contained in a hydrolyzed product-containing solution, alcohols such as for example methanol, ethanol and the like, chain ethers such as for example isopropyl ether and the like, aliphatic hydrocarbons such as for example hexane and the like, water, and the like are listed.

The use amount of the solvent which can deposit the intended lactic acid polymer is usually from 0.1 to 100-fold by weight, preferably from 1 to 10-fold by weight based on the solvent of a hydrolyzed product-containing solution.

As the preferable specific example of combinations of the kind of such solvents and the use amount thereof, there are mentioned, for example, an embodiment in which to a hydrolyzed product-containing solution using as a solvent dichloromethane in an amount of 1 to 5-fold by weight based on the solute, isopropyl ether as a solvent for reducing solubility is used in an amount of 2 to 10-fold by weight based on this dichloromethane, and other embodiments.

The temperature of the solvent when the solvent which can deposit the intended lactic acid polymer solute is brought into contact with a hydrolyzed product-containing solution is usually from −20 to 60° C., preferably from 0 to 40° C., and the temperature of the hydrolyzed product-containing solution is usually from 0 to 40° C., preferably from 10 to 30° C.

As the method of contacting a solvent with a hydrolyzed product-containing solution, a method in which a hydrolyzed product-containing solution is added all at once into a solvent, a method in which a hydrolyzed product-containing solution is dropped into a solvent, a method in which a solvent is added all at once into a hydrolyzed product-containing solution, a method in which a solvent is dropped into a hydrolyzed product-containing solution, and the like are listed.

The lactic acid polymer of the present invention obtained as described above is suitable as a base material for a controlled release composition since the amount of end carboxyl groups is in the range suitable for a base material for a controlled release composition.

The weight ratio of a physiologically active substance in the composition of the present invention differs depending on the kind of a physiologically active substance, desired pharmaceutical effect and duration period of an effect and the like, and in the case of a physiologically active peptide or salt thereof, is from about 0.001 to about 50% by weight, preferably from about 0.02 to about 40% by weight, more preferably about 0.1 to about 30% by weight, further preferably from about 0.1 to about 24% by weight, most preferably from about 3 to about 24% by weight, and in the case of a non-peptide physiologically active substance or salt thereof, from about 0.01 to about 80% by weight, preferably from about 0.1 to about 80% by weight, based on the whole composition.

The weight ratio of a physiologically active substance in the composition of the present invention containing hydroxynaphthoic acid or salt thereof varies depending on the kind of physiologically active substance, desired pharmaceutical effect and duration period of the effect and the like, and in the case of a controlled release composition containing a physiologically active substance or salt thereof, hydroxynaphthoic acid or salt thereof and lactic acid polymer or salt thereof, the weight ratio is, in the case of a physiologically active peptide or salt thereof, from about 0.001 to about 50% by weight, preferably from about 0.02 to about 40% by weight, more preferably about 0.1 to about 30% by weight, most preferably from about 14 to about 24% by weight, and in the case of a non-peptide physiologically active substance or salt thereof, from about 0.01 to about 80% by weight, preferably from about 0.1 to about 50% by weight, based on the sum of three components.

Even if a hydroxynaphthoate which is a physiologically active substance is contained, the same weight ratio is applied. In the case of a controlled release composition containing a salt of a physiologically active peptide (temporarily called (A)) and hydroxynaphthoic acid (temporarily called (B)), the weight ratio of (A) is usually from about 5 to about 90% by weight, preferably from about 10 to about 85% by weight, more preferably from about 15 to about 80% by weight, particularly preferably from about 30 to about 80% by weight, based on the salt of (A) and (B).

In the case of a controlled release composition containing a physiologically active substance or salt thereof, hydroxynaphthoic acid or salt thereof and lactic acid polymer or salt thereof, the compounding amount of hydroxynaphthoic acid or salt thereof is from about ½ to about 2 mol, about ¾ to about ⅘ mol, particularly preferably from about ⅘ to about ⅗ mol, based on one mol of a physiologically active substance or salt thereof.

The design of a composition of the present invention will be described below on a controlled release composition containing a physiologically active substance, hydroxynaphthoic acid and lactic acid polymer wherein the physiologically active substance is basic. In this case, a physiologically active substance as a base and hydroxynaphthoic acid as an acid coexist in the composition, and in either the case of compounding them as free bodies in the composition or the case of compounding them as a salt in the composition, the dissociation equilibrium is satisfied in each case under aqueous conditions or in the presence of a slight amount of water at a certain point in producing the composition. Since the salt formed by hydroxynaphthoic acid which is slightly water-soluble and a physiologically active substance is believed to be slightly water-soluble though varying depending on the property of the physiologically active substance, the dissociation equilibrium shifts to the side of formation of such a slightly water-soluble salt.

For producing a composition containing a basic physiologically active substance in high content, it is desirable that most of the physiologically active substances are protonated to give the above-mentioned slightly water-soluble salt, from the standpoint of the above-mentioned dissociation equilibrium. For this purpose, it is desirable to compound at least a physiologically active substance or salt thereof and approximately equivalent amount of hydroxynaphthoic acid or salt thereof.

Next, the controlled release mechanism of a physiologically active substance contained in the composition will be described below. In the above-mentioned compounding composition, most of physiologically active substances are protonated and exist in the presence of counter ions. Most of the counter ions are hydroxynaphthoic acid (preferably, hydroxynaphthoic acid). After the composition is administered into an organism, oligomers and monomers form due to the decomposition of a lactic acid polymer, however when the polymer is a lactic acid-glycolic acid polymer, the produced oligomer (lactic acid-glycolic acid oligomer) and monomer (lactic acid or glycolic acid) necessarily have one carboxyl group, which also can be counter ions of a physiologically active substance. Release of a physiologically active substance is not accompanied by movement of electric charge, namely, it is released in the form of a salt maintaining a counter ion, and as the movable counter ion species, hydroxynaphthoic acid, lactic acid-glycolic acid oligomer (such molecular weight as to enable movement) and monomer (lactic acid or glycolic acid) are listed, as describe above.

When a plurality of acids coexist, a strongly acidic salt is dominantly formed generally though differing depending on the composition ratio. Regarding the pKa of hydroxynaphthoic acid, for example, 3-hydroxy-2-naphthoic acid has a pKa of 2.708 (CHEMICAL HANDBOOK, BASIC BOOK II, The Chemical Society of Japan, published on Sep. 25, 1969). On the other hand, though pKa of a carboxyl group of a lactic acid-glycolic acid oligomer is not known, it can be calculated based on pKa of lactic acid or glycolic acid (=3.86 or 3.83) according to the principle "change of free energy by introduction of a substituent can be approximated by additive law" Contribution by a substituent to the dissociation constant has been found and can be utilized (Table 4.1 in "pKa Prediction for Organic Acid and Bases", D. D. Perrin, B. Dempsey and E. P. Serjeant, 1981). Since pKas for a hydroxyl group and an ester bond are $\Delta pKa\ (OH)=-0.90$ and $\Delta pKa\ (ester\ bond)=-1.7$ respectively, pKa of a carboxyl group of a lactic acid-glycolic acid oligomer is calculated, in view of contribution by an ester bond nearest to the dissociation group, as follow: pKa=pKa (lactic acid or glycolic acid)−ΔpKa (OH)+ΔpKa (ester bond)=3.06 or 3.03. As a result, since hydroxynaphthoic acid is a stronger acid than lactic acid (pKa=3.86), glycolic acid (pKa=3.83), and further, lactic acid-glycolic acid oligomer, it is supposed that in the above-mentioned composition, a salt of hydroxynaphthoic acid and a physiologically active substance is formed dominantly, and that the property of this salt mainly determines the controlled releasing property of a physiologically active substance in the composition. As the above-mentioned physiologically active substance, the above-mentioned physiologically active substances and the like are listed.

Here, a salt is formed of hydroxynaphthoic acid with a physiologically active substance which is slightly water-soluble but not water-soluble preferably exerts an influence on the controlled release mechanism. That is, as clarified in the consideration of the above-mentioned acid dissociation constant, the salt of hydroxynaphthoic acid which is a stronger acid than the above-mentioned lactic acid-glycolic oligomer and monomer exists dominantly at the initial period of releasing as the hydrolyzable salt of a physiologically active substance, and as a result, the solubility and distribution properties of the salt into body tissue become determining factors of the releasing speed of a physiologically active substance, therefore, the initial releasing pattern of a drug can be controlled by the compounding amount of hydroxynaphthoic acid. Then, with decrease in hydroxynaphthoic acid and increase in oligomers and monomers generated by the hydrolysis of a lactic acid polymer, the releasing mechanism of a physiologically active substance having an oligomer and monomer as counter ions becomes dominant gradually, and even if hydroxynaphthoic acid disappears substantially from the "composition" release of a stable physiologically active substance is retained. Further, enhancement of incorporation efficiency of a physiologically active substance in producing a controlled release composition, and capability of suppression of the initial excess release after administration of a physiologically active substance incorporated can also be explained.

The role of hydroxynaphthoic acid in a controlled release composition containing a hydroxynaphthoate of a physiologically active peptide can also be explained by the above-mentioned mechanism.

The term "water-insolubility" in this specification means a case in which when the above-mentioned substance is stirred at a temperature of 40° C. or lower in distilled water for 4 hours, the weight of a substance dissolved in 1 L of this solution is 25 mg or less.

The term slight water-solubility in this specification means a case in which the above-mentioned weight is over 25 mg and 5 g or less. When the above-mentioned substance is a salt of a physiologically active substance, the weight of a physiologically active substance dissolved in the above-mentioned operation is used for application of the above-mentioned definition.

Though the form of a controlled release composition in this specification is not particularly restricted, the form of a fine particle is preferable, and the form of a microsphere (also called microcapsule in the case of a controlled release composition containing a lactic acid polymer) is particularly preferable. The term microsphere means an injectable fine particle in the form of sphere which can be dispersed in a solution. The verification of the form can be conducted, for example, by observation by a scanning type electron microscope.

The method of producing a controlled release composition (for example, microcapsule) containing the physiologically active substance or salt thereof of the present invention and the lactic acid polymer or salt thereof of the present invention is exemplified below.

In the following production process, drug holding agents (for example, gelatin, salicylic acid and the like) may be added, if necessary, by a method known per se.

(I) In-Water Drying Method
(i) O/W Method

In this method, an organic solvent solution of the lactic acid polymer of the present invention (hereinafter, described as biodegradable polymer of the present invention in some cases) is first produced. The organic solvent used in producing the controlled release composition of the present invention has a boiling point preferably of 120° C. or lower.

As the organic solvent, for example, halogenated hydrocarbons (for example, dichloromethane, chloroform, dichloroethane, trichloroethane, carbon tetrachloride and the like), ethers (for example, ethyl ether, isopropyl ether and the like), fatty esters (for example, ethyl acetate, butyl acetate and the like), aromatic hydrocarbons (for example, benzene, toluene, xylene, and the like), alcohols (for example, ethanol, methanol and the like), acetonitrile and the like are used. Of them, halogenated hydrocarbons are preferable, and particularly, dichloromethane is suitable. These may be used in admixture of appropriate proportion. In this case, mixed solutions of halogenated hydrocarbons and alcohols are preferable, and particularly, a mixed solution of dichloromethane and ethanol is suitable.

The concentration of the biodegradable polymer of the present invention in an organic solvent solution varies depending on the molecular weight of the biodegradable polymer of the present invention and the kind of an organic solvent, and when dichloromethane is used as an organic solvent for example, the concentration is generally from about 0.5 to about 70% by weight, more preferably from about 1 to about 60% by weight, particularly preferably from about 2 to about 50% by weight.

When ethanol is used as an organic solvent mixed with dichloromethane, the ratio of the two solvents is generally from about 0.01 to about 50% (v/v), more preferably from about 0.05 to about 40% (v/v), particularly preferably from about 0.1 to about 30% (v/v).

Into the organic solvent solution of the biodegradable polymer of the present invention thus obtained, a physiologically active substance is added and dissolved or dispersed. In this procedure, the addition amount of a physiologically active substance is controlled so that the upper limit of the weight ratio of physiologically active substance to biodegradable polymer of the present invention is up to about 1:1, preferably up to about 1:2.

Subsequently, the resulting organic solvent solution containing a composition composed of a physiologically active substance or salt thereof and the biodegradable polymer of the present invention are added into a water phase, to form an O (oil phase)/W (water phase) emulsion, then, the solvent in the oil phase is evaporated, to prepare a microcapsule. The volume of the water phase in this case is generally from about 1-fold to about 10000-fold, more preferably from about 5-fold to about 50000-fold, particularly preferably from about 10-fold to about 2000-fold of the oil phase volume.

An emulsifier may be added to the above-mentioned outer water phase. This emulsifier may be any compound providing it can form a generally stable O/W emulsion. Specifically, for example, anionic surfactants (sodium oleate, sodium stearate, sodium laurylsulfate and the like), nonionic surfactants (polyoxyethylene sorbitan fatty esters [Tween 80, Tween 60, manufactured by Atlas Powder] and the like), polyoxyethylene castor oil derivatives [HCO-60, HCO-50, manufactured by NIKKO Chemicals K.K], polyvinylpyrrolidone, polyvinyl alcohol, carboxymethylcellulose, lecithin, gelatin, hyaluronic acid and the like are used. One of them or several of them in combination may be used. The concentration in use is preferably in the range from about 0.01 to 10% by weight, further preferably in the range from about 0.05 to about 5% by weight.

An osmotic pressure controlling agent may be added into the above-mentioned outer water phase. The osmotic pressure controlling agent may be advantageous providing it shows osmotic pressure when made into an aqueous solution.

As the osmotic pressure controlling agent, for example, polyhydric alcohols, monohydric alcohols, monosaccharides, disaccharides, oligosaccharides and amino acids and derivatives thereof and the like are listed.

As the above-mentioned polyhydric alcohols, for example, trihydric alcohols such as glycerin and the like, pentahydric alcohols such as arabitol, xylitol, adonitol and the like, hexahydric alcohols such as mannitol, sorbitol, dulcitol and the like, and other alcohols are used. Of them, hexahydric alcohols are preferable, and particularly, mannitol is suitable.

As the above-mentioned monohydric alcohols, for example, methanol, ethanol, isopropyl alcohol and the like are listed, and of then, ethanol is preferable.

As the above-mentioned monosaccharides, for example, pentoses such as arabinose, xylose, ribose, 2-deoxyribose and the like, and hexoses such as glucose, fructose, galactose, mannose, sorbose, rhamnose, fucose and the like are used, and of then, hexoses are preferable.

As the above-mentioned oligosaccharides, for example, trioses such as maltotriose, raffinose and the like, tetroses such as stachyose and the like are used, and of them, trioses are preferable.

As the derivatives of the above-mentioned monosaccharides, disaccharides and oligosaccharides, for example, glucosamine, galactosamine, glucuronic acid, galacturonic acid and the like are used.

Any of the above-mentioned amino acids may be used providing they are L-amino acids, and for example, glycine, leucine, arginine and the like are listed. Of them, L-arginine is preferable.

These osmotic pressure controlling agents may be used alone or in admixture.

These osmotic pressure controlling agents are used in concentrations so that the osmotic pressure of the outer water phase is from about 1/50 to about 5-fold, preferably from about 1/25 to about 3-fold of the osmotic pressure of physiological saline. When mannitol is used as an osmotic pressure regulating agent, its concentration is preferably 0.5% to 1.5%.

As the method of removing an organic solvent, a method known per se or pursuant method is used. For example, a method in which an organic solvent is evaporated while stirring by a propeller type stirrer or magnetic stirrer and the like at normal pressure or reduced pressure gradually reduced, a method in which an organic solvent is evaporated while controlling the degree of vacuum using a rotary evaporator and the like, and other methods are listed.

Thus obtained microcapsule is separated by centrifugation or filtration, then, free physiologically active substances, emulsifier and the like adhered to the surface of a microcapsule are washed several times repeatedly with distilled water, dispersed again into distilled water and the like and freeze-dried.

In the production process, a coagulation preventing agent may be added for preventing mutual coagulation of particles. As the coagulation preventing agent, for example, water-soluble polysaccharides such as mannitol, lactose, glucose, starches (for example, corn starch and the like) and the like, amino acids such as glycine and the like, proteins such as fibrin, collagen and the like, are used. Of them, mannitol is suitable.

The addition amount of the coagulation preventing agent such as mannitol and the like is usually from 0 to about 24% by weight based on the microcapsule total weight.

After freeze drying, if necessary, water and an organic solvent in microcapsules may be removed by heating under conditions causing no mutual fusion of microcapsules under reduced pressure. Preferably, microcapsules are heated at a temperature around or slightly higher than the intermediate point glass transition temperature of an biodegradable polymer measured by a differential scanning calorimeter under conditions of a temperature increasing speed of 10 to 20° C. per minute. More preferably, heating is conducted at temperatures around the intermediate point glass transition temperature of an biodegradable polymer or within the range from the intermediate point glass transition temperature thereof to a temperature higher by about 30° C. than the intermediate point glass transition temperature. Particularly, when a lactic acid-glycolic acid polymer is used as an biodegradable polymer, heating is conducted preferably at temperatures lying within the range from around the intermediate point glass transition temperature to a temperature higher than the intermediate point glass transition temperature by 10° C., further preferably at temperatures lying within the range from around the intermediate point glass transition temperature to a temperature higher than the intermediate point glass transition temperature by 5° C.

Though the heating time varies depending on the amount of microcapsules and the like, it is from about 12 hours to about 168 hours, preferably from about 24 hours to about 120 hours, particularly preferably from about 48 hours to about 96 hours, after the microcapsule itself reaches a given temperature.

The heating method is not particularly restricted provided that a set of microcapsules can be uniformly heated.

As the heat drying method, for example, a method of heat drying in a constant temperature chamber, fluidized chamber, moving chamber or kiln, a method of heat drying by microwave, and the like are used. Among them, a method of heat drying in a constant temperature chamber is preferable.

(ii) W/O/W Method

First, an organic solvent solution of the biodegradable polymer of the present invention is produced.

As the organic solvent, for example, halogenated hydrocarbons (for example, dichloromethane, chloroform, dichloroethane, trichloroethane, carbon tetrachloride and the like), ethers (for example, ethyl ether, isopropyl ether and the like), fatty esters (for example, ethyl acetate, butyl acetate and the like), aromatic hydrocarbons (for example, benzene, toluene, xylene, and the like), alcohols (for example, ethanol, methanol and the like), acetonitrile and the like are used. Of them, halogenated hydrocarbons are preferable, and particularly, dichloromethane is suitable. These may be used in admixture of appropriate proportion. In this case, mixed solutions of halogenated hydrocarbons and alcohols are preferable, and particularly, a mixed solution of dichloromethane and ethanol is suitable.

The concentration of the biodegradable polymer of the present invention in an organic solvent solution varies depending on the molecular weight thereof and the kind of an organic solvent, and when dichloromethane is used as an organic solvent for example, the concentration is generally from about 0.5 to about 70% by weight, more preferably from about 1 to about 60% by weight, particularly preferably from about 2 to about 50% by weight.

Subsequently, a solution of a physiologically active substance or salt thereof [as the solvent, water, a mixed solution of water and alcohols (for example, methanol, ethanol and the like)] is added to an organic solvent solution (oil phase) of the biodegradable polymer of the present invention. This mixture is emulsified by a known method by a homogenizer or ultrasond and the like, to form a W/O emulsion.

A volume of an oily phase to be mixed is about 1 to about 1000-fold, preferably 2 to 100-fold, more preferably about 3 to 10-fold relative to a volume of an inner aqueous phase.

A range of the viscosity of the resulting W/O emulsion is generally about 10 to 10,000 cp, preferably about 100 to 5,000 cp, particularly preferably about 500 to 2,000 cp at about 12 to 25° C.

Then, the resultant W/O emulsion composed of a physiologically active substance and the biodegradable polymer of the present invention are added into a water phase, to form a W (inner water phase)/O (oil phase)/W (outer water phase), then, solvent in the oil phase is evaporated to prepare a microcapsule. In this operation, the volume of the outer water phase is generally from about 1-fold to about 10000-fold, more preferably from about 5-fold to about 50000-fold, particularly preferably from about 10-fold to about 2,000-fold of the oil phase volume.

The above-mentioned emulsifier, osmotic pressure controlling agent which may be added into the outer water phase and the subsequent preparation method are the same as in section (I)(i).

(II) Phase Separation Method

When a microcapsule is produced by this method, a coacervation agent is gradually added while stirring into an organic solvent solution containing a composition composed of the physiologically active substance described in the in-water drying method of section (I) and the biodegradable polymer of the present invention, to precipitate and solidify a microcapsule. The amount of the coacervation agent is from about 0.01 to 1000-fold, preferably from about 0.05 to 500-fold, particularly preferably from about 0.1 to 200-fold of the oil phase volume.

The coacervation agent is not particularly restricted providing that it is selected from polymer-based, mineral oil-based or vegetable oil-based compounds which are miscible with an organic solvent and do not dissolve the biodegradable polymer of the present invention. Specifically, for example, silicon oil, sesame oil, soy bean oil, corn oil, cotton seed oil, coconut oil, linseed oil, mineral oil, n-hexane, n-heptane and the like are used. These may be used in admixture of two or more agents.

The thus obtained microcapsule is separated, then, washed with heptane repeatedly to remove the coacervation agent and the like other than the composition composed of the physiologically active substance and the biodegradable polymer of the present invention, and the residue is dried under reduced pressure. Alternatively, washing is effected in the same manner as in the above-mentioned in-water drying method of section (I)(i), then, freeze-dried, further, dried under heat.

(III) Spray Drying Method

For producing a microcapsule by this method, an organic solvent solution or dispersion containing a composition composed of the biodegradable polymer of the present invention and the physiologically active substance described in the above-mentioned in-water drying method of section (I) is sprayed into a drying room of a spray drier (spray drying machine) using a nozzle, and an organic solvent in micronized liquid drops is evaporated in an extremely short period of time, to prepare a microcapsule. As this nozzle, for example, bi-fluid nozzle type, pressure nozzle type, rotation disk type and the like are mentioned. After this, if necessary, washing may be effected in the same manner as in the above-mentioned in-water drying method of (I), then, freeze-dried, further, dried under heat.

Regarding the agent form other than the above-mentioned microcapsule, an organic solvent solution or dispersion containing a composition composed of the physiologically active substance described in the in-water drying method in the microcapsule production method (I) and the biodegradable polymer of the present invention may be dried to solid by evaporating an organic solvent or water while controlling the degree of vacuum using a rotary evaporator, then, ground by a jet mill and the like to give fine particles (micro particles).

Further, the finely ground particles may be washed in the same manner as in the in-water drying method of the microcapsule production method (I), then, freeze-dried, further, dried under heat.

The method of producing a controlled release composition (for example, microcapsule) containing the physiologically active substance or salt thereof of the present invention, hydroxynaphthoic acid or salt thereof and the lactic acid polymer or salt thereof of the present invention is exemplified below, however, also in the case without inclusion of hydroxynaphthoic acid or salt thereof, production can be effected in the same manner.

(I) In-Water Drying Method (i) O/W Method

In this method, an organic solvent solution of hydroxynaphthoic acid or salt thereof and a lactic acid polymer or salt thereof is first produced. The organic solvent used in producing the controlled release composition of the present invention has a boiling point preferably of 120° C. or lower.

As the organic solvent, for example, halogenated hydrocarbons (for example, dichloromethane, chloroform, dichloroethane, trichloroethane, carbon tetrachloride and the like), ethers (for example, ethyl ether, isopropyl ether and the like), fatty esters (for example, ethyl acetate, butyl acetate and the like), aromatic hydrocarbons (for example, benzene, toluene, xylene, and the like), alcohols (for example, ethanol, methanol and the like), acetonitrile and the like are used. As the organic solvent for a lactic acid polymer or salt thereof, dichloromethane is particularly suitable.

As the organic solvent for hydroxynaphthoic acid or salt thereof, alcohols are preferable. These may be separately dissolved before mixing, or two materials may be dissolved in an organic solvent mixed in suitable proportion. Of them, mixed solutions of halogenated hydrocarbons and alcohols are preferable, and particularly, a mixed solution of dichloromethane and ethanol is suitable.

When ethanol is used as an organic solvent mixed with dichloromethane, the content of ethanol in a mixed organic solvent of dichloromethane and ethanol is generally from about 0.01 to about 50% (v/v), more preferably from about 0.05 to about 40% (v/v), particularly preferably from about 0.1 to about 30% (v/v).

The concentration of a lactic acid polymer in an organic solvent solution varies depending on the molecular weight of the lactic acid polymer and the kind of an organic solvent, and when dichloromethane is used as an organic solvent for example, the concentration is generally from about 0.5 to about 70% by weight, more preferably from about 1 to about 60% by weight, particularly preferably from about 2 to about 50% by weight.

The concentration of hydroxynaphthoic acid or salt thereof in an organic solvent is, when a mixture of dichloromethane and ethanol is used as an organic solvent, generally from about 0.01 to about 10% by weight, more preferably from about 0.1 to about 5% by weight, particularly preferably from about 0.5 to about 3% by weight.

Into the organic solvent solution of hydroxynaphthoic acid or salt thereof and a lactic acid polymer thus obtained, a physiologically active substance or salt thereof is added and dissolved or dispersed. Subsequently, the resultant organic solvent solution containing composition composed of a physiologically active substance or salt thereof, hydroxynaphthoic acid or salt thereof, and lactic acid polymer or salt thereof is added into a water phase, to form an O (oil phase)/W (water phase) emulsion, then, a solvent in the oil phase is evaporated or dispersed in the water phase, to prepare a microcapsule. The volume of the water phase in this case is generally from about 1-fold to about 10000-fold, more preferably from about 5-fold to about 50000-fold, particularly preferably from about 10-fold to about 2000-fold of the oil phase volume.

An emulsifier may be added to the above-mentioned outer water phase. This emulsifier may be any compound providing it can form a generally stable O/W emulsion. Specifically, for example, anionic surfactants (sodium oleate, sodium stearate, sodium laurylsulfate and the like), nonionic surfactants (polyoxyethylene sorbitan fatty esters [Tween 80, Tween 60, manufactured by Atlas Powder], polyoxyethylene castor oil derivatives [HCO-60, HCO-50, manufactured by Nikko Chemicals] and the like), polyvinylpyrrolidone, polyvinyl alcohol, carboxymethylcellulose, lecithin, gelatin, hyaluronic acid and the like are used. One of them or several of them in combination may be used. The concentration in use is preferably in the range from about 0.01 to 10% by weight, further preferably in the range from about 0.05 to about 5% by weight.

An osmotic pressure controlling agent may be added into the above-mentioned outer water phase. The osmotic pressure controlling agent may be advantageous providing it shows osmotic pressure when made into an aqueous solution.

As the osmotic pressure controlling agent, for example, polyhydric alcohols, monohydric alcohols, monosaccharides, disaccharides, oligosaccharides and amino acids and derivatives thereof and the like are listed.

As the above-mentioned polyhydric alcohols, for example, trihydric alcohols such as glycerin and the like, pentahydric alcohols such as arabitol, xylitol, adonitol and the like, hexahydric alcohols such as mannitol, sorbitol, dulcitol and the like, and other aldohols are used. Of them, hexahydric alcohols are preferable, and particularly, mannitol is suitable.

As the above-mentioned monohydric alcohols, for example, methanol, ethanol, isopropyl alcohol and the like are listed, and of then, ethanol is preferable.

As the above-mentioned monosaccharides, for example, pentoses such as arabinose, xylose, ribose, 2-deoxyribose and the like, and hexoses such as glucose, fructose, galactose, mannose, sorbose, rhamnose, fucose and the like are used, and of then, hexoses are preferable.

As the above-mentioned oligosaccharides, for example, trioses such as maltotriose, raffinose and the like, tetroses such as stachyose and the like are used, and of them, trioses are preferable.

As the derivatives of the above-mentioned monosaccharides, disaccharides and oligosaccharides, for example, glucosamine, galactosamine, glucuronic acid, galacturonic acid and the like are used.

Any of the above-mentioned amino acids may be used providing they are L-amino acids, and for example, glycine, leucine, arginine and the like are listed. Of them, L-arginine is preferable.

These osmotic pressure controlling agents may be used alone or in admixture.

These osmotic pressure controlling agents are used in concentrations so that the osmotic pressure of the outer water phase is from about 1/50 to about 5-fold, preferably from about 1/25 to about 3-fold of the osmotic pressure of physiological saline. When mannitol is used as an osmotic pressure regulating agent, its concentration is preferably 0.5% to 1.5%.

As the method of removing an organic solvent, a method known per se or pursuant method is used. For example, a method in which an organic solvent is evaporated while stirring by a propeller type stirrer or magnetic stirrer, ultrasonic wave generating apparatus and the like at normal pressure or reduced pressure gradually reduced, a method in which an organic solvent is evaporated while controlling the degree of vacuum using a rotary evaporator and the like, a method in which an organic solvent is gradually removed using a dialysis film, and other methods are listed.

The thus obtained microcapsule is separated by centrifugation or filtration, then, free physiologically active substances or salt thereof, hydroxynaphthoic acid or salt thereof, drug holding substance, emulsifier and the like adhered to the surface of a microcapsule are washed several times repeatedly with distilled water, dispersed again into distilled water and the like and freeze-dried.

In the production process, a coagulation preventing agent may be added for preventing mutual coagulation of particles. As the coagulation preventing agent, for example, water-soluble polysaccharides such as mannitol, lactose, glucose, starches (for example, corn starch and the like) and the like, amino acids such as glycine and the like, proteins such as fibrin, collagen and the like, are used. Of them, mannitol is suitable.

The addition amount of the coagulation preventing agent such as mannitol and the like is usually from 0 to about 24% by weight based on the microcapsule total weight.

After freeze drying, if necessary, water and an organic solvent in microcapsules may be removed by heating under conditions causing no mutual fusion of microcapsules under reduced pressure. Preferably, microcapsules are heated at a temperature around or slightly higher than the intermediate point glass transition temperature of a lactic acid polymer measured by a differential scanning calorimeter under conditions of a temperature increasing speed of 10 to 20° C. per minute. More preferably, heating is conducted at temperatures around the intermediate point glass transition temperature of a lactic acid polymer or within the range from the intermediate point glass transition temperature of a lactic acid polymer to a temperature higher by about 30° C. than the intermediate point glass transition temperature thereof. Particularly, when a lactic acid-glycolic acid polymer is used as a lactic acid polymer, heating is conducted preferably at temperatures lying within the range from around the intermediate point glass transition temperature to a temperature higher than the intermediate point glass transition temperature by 10° C., further preferably at temperatures lying within the range from around the intermediate point glass transition temperature to a temperature higher than the intermediate point glass transition temperature by 5° C.

Though the heating time varies depending on the amount of microcapsules and the like, it is from about 12 hours to about 168 hours, preferably from about 24 hours to about 120 hours, particularly preferably from about 48 hours to about 96 hours, after the microcapsule itself reaches a given temperature.

The heating method is not particularly restricted provided that a set of microcapsules can be uniformly heated.

As the heat drying method, for example, a method of heat drying in a constant temperature chamber, fluidized chamber, moving chamber or kiln, a method of heat drying by microwave, and the like are used. Among them, a method of heat drying in a constant temperature chamber is preferable.

(ii) W/O/W Method (1)

First, an organic solvent solution of a lactic acid polymer or salt thereof is produced.

The organic solvent and the concentration of a lactic acid polymer or salt thereof in the organic solvent solution are the same as in the above-mentioned section (I)(i). When a mixed organic solvent is used, the proportion of the two materials is the same as in the above-mentioned section (I)(i).

A physiologically active substance or salt thereof is dissolved or dispersed in thus obtained organic solvent solution of a lactic acid polymer or salt thereof. Then, to the organic solvent solution (oil phase) containing a composition composed of a physiologically active substance or salt thereof and a lactic acid polymer or salt thereof, a solution of hydroxynaphthoic acid or salt thereof [as the solvent, water, aqueous solution of alcohols (for example, methanol, ethanol and the like), pyridine aqueous solution, dimethylacetamide aqueous solution and the like] is added. This mixture is emulsified by a known method by a homogenizer or ultrasond and the like, to form a W/O emulsion.

Then, the resulting W/O emulsion composed of a physiologically active substance or salt thereof, hydroxynaphthoic acid or salt thereof and a lactic acid polymer or salt thereof is added into a water phase, to form a W (inner water phase)/O (oil phase)/W (outer water phase), then, a solvent in the oil phase is evaporated to prepare a microcapsule. In this operation, the volume of the outer water phase is generally from about 1-fold to about 10000-fold, more preferably from about 5-fold to about 5000-fold, particularly preferably from about 10-fold to about 2000-fold of the oil phase volume.

The above-mentioned emulsifier, osmotic pressure controlling agent which may be added into the outer water phase and the subsequent preparation method are the same as in the section (I)(i).

(iii) W/O/W Method (2)

First, an organic solvent solution of hydroxynaphthoic acid or salt thereof and a lactic acid polymer or salt thereof is produced, and thus obtained organic solvent solution is called an oil phase. This production method is the same as in the above-mentioned section (I)(i). Alternatively, hydroxynaphthoic acid or salt thereof and a lactic acid polymer may be separately produced as organic solvent solutions before their mixing. The concentration of a lactic acid polymer in an organic solvent solution varies depending on the molecular weight of the lactic acid polymer and the kind of organic solvent, and when dichloromethane is used as an organic solvent for example, the concentration is generally from about 0.5 to about 70% by weight, more preferably from about 1 to about 60% by weight, particularly preferably from about 2 to about 50% by weight.

Next, a solution or dispersion of a physiologically active substance or salt thereof [as the solvent, water, mixtures of water and alcohols (for example, methanol, ethanol and the like) and the like] is produced.

The addition concentration of a physiologically active substance or salt thereof is generally from 0.001 mg/ml to 10 g/ml, more preferably from 0.1 mg/ml to 5 g/ml, further preferably from 10 mg/ml to 3 g/ml.

When the above-described physiologically active substance has a basic group such as amino group, salts of a physiologically active substance include a salt with inorganic acid (also referred to as inorganic free acid) (for example, carbonic acid, acid carbonate, hydrochloric acid, sulfuric acid, nitric acid, boric acid etc.), organic acid (also referred to as organic free acid) (for example, succinic acid, acetic acid, propionic acid, trifluoracetic acid etc.).

When a physiologically active substance has a acidic group such as carboxyl group, salts of a physiologically active substance include a salt with inorganic base (also referred to as inorganic free base) (for example, alkali metals such as sodium, potassium, alkali earth metals such as calcium, magnesium, etc.), organic base (also referred to as organic free base) (for example, organic amines such as triethylamine, basic amino acids such as arginine, etc.). Further, physiologically active peptides may form a metal complex compound (for example, copper complex, zinc complex etc.). When a physiologically active substance is a LHRH derivative, acetic acid is particularly preferably added.

As the solution aid and stabilizer, known materials may be used. Heating, shaking, stirring and the like may be conducted for dissolution and dispersion of a physiologically active substance and additives to an extent not deteriorating activity, and thus obtained aqueous solution is called inner water phase.

The inner water phase and oil phase obtained described above were emulsified by a known method such as homogenizer or ultrasonic wave and the like to form a W/O emulsion.

The volume of the oil phase mixed is from about 1 to about 1000-fold, preferably from 2 to 100-fold, more preferably from about 3 to 10-fold of the volume of the inner water phase.

The viscosity of the resulted W/O emulsion is generally from about 10 to 10000 cp, preferably from about 100 to 5000 cp, further preferably from about 500 to 2000 cp at from about 12 to 25° C.

Then, the resultant W/O emulsion composed of a physiologically active substance or salt thereof, hydroxynaphthoic acid or salt thereof and a lactic acid polymer or salt thereof is added into a water phase, to form a W (inner water phase)/O (oil phase)/W (outer water phase), then, a solvent in the oil phase is evaporated or scattered into the outer water phased, to prepare a microcapsule. In this operation, the volume of the outer water phase is generally from about 1-fold to about 10000-fold, more preferably from about 5-fold to about 5000-fold, particularly preferably from about 10-fold to about 2000-fold of the oil phase volume.

The above-mentioned emulsifier, osmotic pressure controlling agent which may be added into the outer water phase and the subsequent preparation method are the same as in section (I)(i).

(II) Phase Separation Method

When a microcapsule is produced by this method, a coacervation agent is gradually added while stirring into an organic solvent solution containing a composition composed of the physiologically active substance or salt thereof described in the in-water drying method of (I), hydroxynaphthoic acid or salt thereof and lactic acid polymer or salt thereof, to precipitate and solidify a microcapsule. The amount of the coacervation agent is from about 0.01 to 1000-fold, preferably from about 0.05 to 500-fold, particularly preferably from about 0.1 to 200-fold of the oil phase volume.

The coacervation agent is not particularly restricted providing that it is selected from polymer-based, mineral oil-based or vegetable oil-based compounds which are miscible with an organic solvent but do not dissolve the physiologically active substance or salt thereof, hydroxynaphthoic acid or salt thereof and lactic acid polymer or salt thereof. Specifically, for example, silicon oil, sesame oil, soy bean oil, corn oil, cotton seed oil, coconut oil, linseed oil, mineral oil, n-hexane, n-heptane and the like are used. These may be used in admixture of two or more agents.

Thus obtained microcapsule is separated, then washed with heptane repeatedly to remove the coacervation agent and the like other than the composition composed of the physiologically active substance or salt thereof, hydroxynaphthoic acid or salt thereof and lactic acid polymer or salt thereof, and the residue is dried under reduced pressure. Alternatively, washing is effected in the same manner as in the above-mentioned in-water drying method of section (I)(i), then, freeze-dried, further, dried under heat.

(III) Spray Drying Method

For producing a microcapsule by this method, an organic solvent solution containing the physiologically active substance or salt thereof, hydroxynaphthoic acid or salt thereof and lactic acid polymer or salt thereof described in the above-mentioned in-water drying method of (I) is sprayed into a drying room of a spray drier (spray drying machine) using a nozzle, and an organic solvent in a micronized liquid drop is evaporated in an extremely short period of time, to prepare a microcapsule. As this nozzle, for example, bi-fluid nozzle type, pressure nozzle type, rotation disk type and the like are mentioned. After this, if necessary, washing may be effected in the same manner as in the above-mentioned in-water drying method of (I), then, freeze-dried, further, dried under heat.

Regarding the form other than the above-mentioned microcapsule, the organic solvent solution containing the physiologically active substance or salt thereof, hydroxynaphthoic acid or salt thereof and lactic acid polymer or salt thereof described in the in-water drying method in the microcapsule production method (I) may be dried to solid by evaporating an organic solvent or water while controlling the degree of vacuum using a rotary evaporator and the like, then, ground by a jet mill and the like to give fine particles (also called micro particles).

Further, the finely ground particles may be washed in the same manner as in the in-water drying method of the microcapsule production method (I), then, freeze-dried, further, dried under heat.

The microcapsule or fine powder thus obtained can provide drug release corresponding to the decomposition speed of a lactic acid polymer or lactic acid-glycolic acid polymer used.

Then, the method of producing a controlled release composition containing a hydroxynaphthoate which is a physiologically active substance of the present invention will be exemplified. In the production method, a physiologically active peptide is preferably used as the physiologically active substance.

(IV) Two Step Method

A physiologically active substance or salt thereof is added to an organic solvent solution of hydroxynaphthoic acid or salt thereof so that the weight ratio shown in the above-mentioned definition of the compounding amount of a physiologically active substance is satisfied, to make an organic solvent solution containing a hydroxynaphthoate of a physiologically active substance.

This organic solvent is the same as described in section (I)(i). When a mixed organic solvent is used, the ratio of the two solvents is the same as described in the above-mentioned section (I)(i).

As the method of removing an organic solvent for precipitating a composition containing a hydroxynaphthoate which is a physiologically active substance, a method known per se or pursuant method is used. For example, a method in which an organic solvent is evaporated while controlling the degree of vacuum using a rotary evaporator and the like, and other methods are listed.

The organic solvent solution of a composition containing a hydroxynaphthoate which is a physiologically active substance thus obtained is produced again, and a controlled release composition (microsphere of fine particle) can be produced.

As the organic solvent, for example, halogenated hydrocarbons (for example, dichloromethane, chloroform, dichloroethane, trichloroethane, carbon tetrachloride and the like), ethers (for example, ethyl ether, isopropyl ether and the like), fatty esters (for example, ethyl acetate, butyl acetate and the like), aromatic hydrocarbons (for example, benzene, toluene, xylene, and the like) and the like are used. These may be used in admixture of appropriate proportion. Of them, halogenated hydrocarbons are preferable, and particularly, dichloromethane is suitable.

Next, the resultant organic solvent solution containing a composition containing a hydroxynaphthoate of a physiologically active substance is added into a water phase, to form an O (oil phase)/W (water phase) emulsion, then, a solvent in the oil phase is evaporated, to prepare a microcapsule. The volume of the water phase in this case is generally from about 1-fold to about 10000-fold, more preferably from about 5-fold to about 5000-fold, particularly preferably from about 10-fold to about 2000-fold of the oil phase volume.

The above-mentioned emulsifier, osmotic pressure controlling agent which may be added into the outer water phase and the subsequent preparation method are the same as in section (I)(i).

As the method of removing an organic solvent, a method known per se or pursuant method is used. For example, a method in which an organic solvent is evaporated while stirring by a propeller type stirrer or magnetic stirrer and the like at normal pressure or reduced pressure gradually reducing, a method in which an organic solvent is evaporated while controlling the degree of vacuum using a rotary evaporator and the like, and other methods are listed.

The thus obtained microsphere is separated by centrifugation or filtration, then, free physiologically active substances, hydroxynaphthoic acid, emulsifier and the like adhered to the surface of a microsphere are washed several times repeatedly with distilled water, dispersed again into distilled water and the like and freeze-dried.

In the production process, a coagulation preventing agent may be added for preventing mutual coagulation of particles. As the coagulation preventing agent, for example, water-soluble polysaccharides such as mannitol, lactose, glucose, starches (for example, corn starch and the like) and the like, amino acids such as glycine and the like, proteins such as fibrin, collagen and the like, are used. Of them, mannitol is suitable.

Further, after freeze drying, if necessary, water and an organic solvent in microspheres may be removed by heating under conditions causing no mutual fusion of microspheres under reduced pressure.

Though the heating time varies depending on the amount of microspheres and the like, it is from about 12 hours to about 168 hours, preferably from about 24 hours to about 120 hours, particularly preferably from about 48 hours to about 96 hours, after the microsphere itself reaches a given temperature.

The heating method is not particularly restricted provided that a set of microcapsules can be uniformly heated.

As the heat drying method, for example, a method of heat drying in a constant temperature chamber, fluidized chamber, moving chamber or kiln, a method of heat drying by microwave, and the like are used. Among them, a method of heat drying in a constant temperature chamber is preferable. The resultant microsphere is in the form of relatively uniform sphere, causes little resistance in injection administration, and does not cause needle clogging easily. Since a slim injection needle can be used, injection into a patient is less painful.

(V) One Step Method

A physiologically active substance or salt thereof is added to an organic solvent solution of hydroxynaphthoic acid or salt thereof so that the weight ratio shown in the above-mentioned definition of the compounding amount of a physiologically active substance is satisfied, to make an organic solvent solution containing a hydroxynaphthoate of a physiologically active substance, and a controlled release composition (microsphere or fine particle) is produced.

This organic solvent is the same as described in section (I)(i). When a mixed organic solvent is used, the ratio of them is the same as described in the above-mentioned section (I)(i).

Next, an organic solvent solution containing a hydroxynaphthoate of a physiologically active substance is added into a water phase, to form an O (oil phase)/W (water phase) emulsion, then, a solvent in the oil phase is evaporated, to prepare a microsphere. The volume of the water phase in this case is generally from about 1-fold to about 10000-fold, more preferably from about 5-fold to about 5000-fold, particularly preferably from about 10-fold to about 2000-fold of the oil phase volume.

The above-mentioned emulsifier, osmotic pressure controlling agent which may be added into the outer water phase and the subsequent preparation method are the same as in section (IV).

The controlled release composition of the present invention may be any form such as microsphere, microcapsule, fine particle (micro particle) and the like, and a microcapsule is suitable.

The controlled release composition of the present invention can be administered itself or can be used as a raw material substance and made into various drug forms before administration, as an injection or implantable agent into muscle, subcutaneous, organs and the like, permucosal agents into nose, rectum, uterus and the like, oral agents (for example, capsules (hard capsule, soft capsule and the like), solid drugs such as granules, powder and the like, liquid drugs such as syrup, emulsion, suspension and the like) and the like.

For example, for use of the controlled release compositions of the present invention as an injection, these can be made into an aqueous suspension together with a dispersing agent (for example, surfactants such as Tween 80, HCO-60 and the like, polysaccharides such as sodium hyaluronate, carboxymethylcellulose, sodium alginate and the like), preservative (for example, methylparaben, propylparaben and the like), isotonization agent (for example, sodium chloride, mannitol, sorbitol, glucose, proline and the like), or dispersed together with vegetable oil such as sesame oil, corn oil and the like to give an oily suspension, which can be actually used as a controlled release injection.

The particle size of the controlled release composition of the present invention, when used as a suspended injection, may advantageously be in the range satisfying the degree of dispersion and needle passing property, and for example, from about 0.1 to 300 μm, preferably from about 0.5 to 150 μm, further preferably from about 1 to 100 μm as the average particle size.

For sterilizing the controlled release composition of the present invention, a method of sterilizing the production whole process, a method of sterilization by γ-ray, a method of adding a preservative, and the like are listed, but the sterilization method is not limited to them.

The controlled release composition of the present invention can be used as a safe medicine and the like for mammals (for example, human, cattle, pig, dog, cat, mouse, rat, rabbit and the like) since it has low toxicity.

The dosage of the controlled release composition of the present invention differs variously depending on the kind and content of a physiologically active substance which is the main drug, drug form, duration time of release of a physiologically active substance, object diseases, object animals and the like, and may advantageously be the effective amount of a physiologically active substance. The dose per administration of a physiologically active substance which is a main drug is, when the controlled release composition is 6-month preparation, selected preferably within the range from about 0.01 mg to 10 mg/kg, further preferably within the range from about 0.05 mg to 5 mg/kg per adult person.

The dose of the controlled release composition per administration is selected in the range of preferably from about 0.05 mg to 50 mg/kg, further preferably from about 0.1 mg to 30 mg/kg per one adult.

The dose frequency can be appropriately selected depending on the kind and content of a physiologically active substance which is the main drug, drug form, duration time of release of a physiologically active substance, object diseases, object animals and the like, such as once per several weeks, once per month, once per several months (for example, 3, 4 or 6 months, and the like) and the like.

The controlled release composition of the present invention can be used as a preventive or curative agent for various diseases depending on the kind of a physiologically active substance contained, and when the physiologically active substance is a LH-RH derivative for example, can be used as a preventive or curative drug for hormone-dependent diseases, particularly, sex hormone-dependent diseases such as sex hormone-dependent cancers (e.g., prostatic cancer, uterine cancer, breast cancer, pituitary tumor and the like), prostatic hyperplasia, endometriosis, uterine myoma, precocious puberty, dysmenorrhea, amenorrhea, premenstrual syndrome, multilocular ovary syndrome and the like, as a preventive drug for recurrence of breast cancer after the operation for premenopausal breast cancer, as a preventive or curative drug for Alzheimer disease and immune deficiency and the like, and as a contraceptive agent (or, when rebound effect after drug withdrawal is utilized, prevention and curing of infertility), and the like. Further, the controlled release composition of the present invention can be used also as a preventive or curative drug for benign or malignant tumor which is LH-RH dependent though sex hormone non-dependent.

Therefore, hormone dependent diseases, in particular, sex hormone dependent cancers (for example, prostate cancer, uterine cancer, breast cancer, pituitary gland tumor and the like), sex hormone dependent diseases such as prostatomegaly, endometriosis, hysteromyoma, precocious puberty, dysmenorrhea, amenorrhea, premenstrual syndrome, multilocular ovary syndrome and the like can be prevented or treated; and pregnancy can be prevented by administering to a mammal an effective dose of the treating or preventing agent according to this invention, and also recurrence of breast cancer after the operation for premenopausal breast cancer can be prevented thereby.

The following examples and reference examples will illustrate the present invention in detail, but do not limit the scope of the invention at all.

EXAMPLES

The weight-average molecular weight and the content of each polymer in the following examples and reference examples are the weight-average molecular weight in terms of polystyrene measured by gel permeation chromatography (GPC) using mono-dispersed polystyrene as a standard substance and the content of each polymer calculated from it. Measurements were all conducted by a high performance GPC apparatus (manufactured by Tosoh Corp.; HLC-8120 GPC), and Super H 4000×2 and Super H 2000 (all manufactured by Tosoh Corp.) were used as the column and tetrahydrofuran was used at a flow rate of 0.6 mL/min as the mobile phase. The detection method is based on differential refractive index.

Reference Example A1

Synthesis of Lactic Acid Polymer of Higher Molecular Weight

To 230 mL of dehydrated xylene was added 4.1 mL of 1.0 mol/L diethylzinc hexane solution, 1.35 g of tert-butyl lactate and 230 g of DL-lactide, and they were polymerization-reacted at 120 to 130° C. for about 2 hours. After completion of the reaction, 120 mL of dichloromethane was poured into the reaction solution, and to this was added 230 mL of trifluoroacetic acid to case a deprotection reaction. After completion of the reaction, 300 mL of dichloromethane was added to the reaction solution, then, the reaction solution was poured into 2800 mL of isopropyl ether to cause precipitation of the intended substance, then, a re-precipitation operation was repeated with dichloromethane/isopropyl ether, to obtain a lactic acid polymer having a weight-average molecular weight of about 40000.

Reference Example B1

The polymer obtained in Reference Example A1 was dissolved in 600 mL of dichloromethane, and washed with water until the solution became neutral, then, 70 g of a 90% lactic acid aqueous solution was added, and they were reacted at 40° C. When the weight-average molecular weight of the polymer dissolved in the reaction solution reached about 20000, the solution was cooled to room temperature, and 600 mL of dichloromethane was poured to stop the reaction, and the solution was washed with water until the reaction solution became neutral. After washing with water, the reaction solution was concentrated and dried to obtain a lactic acid polymer. The amount of the end carboxyl groups of the resulting lactic acid polymer was about 80 μmol per 1 g of the polymer, and the content of polymers having molecular weights of 5000 or less was 7.29 wt %.

Reference Example C1

The polymer obtained in Reference Example A1 was dissolved in 600 mL of dichloromethane, and washed with water until the solution became neutral, then, 70 g of a 90% lactic acid aqueous solution was added, and they were reacted at 40° C. When the weight-average molecular weight of the polymer dissolved in the reaction solution reached about 20000, the solution was cooled to room temperature, and 600 mL of dichloromethane was poured to stop the reaction, and the solution was washed with water until the reaction solution became neutral, then, the reaction solution was dropped into 2800 mL of isopropyl ether, to cause precipitation of the intended lactic acid polymer. The precipitate obtained by decantation was dissolved in 600 mL of dichloromethane, then, the solution was concentrated and dried to obtain 160 g of a lactic acid polymer. The amount of the end carboxyl groups of the resultant lactic acid polymer was about 70 μmol per 1 g of the polymer. The weight-average molecular weight of the lactic acid polymer of higher molecular weight used, the weight-average molecular weight of the lactic acid polymer after hydrolysis treatment, the weight-average molecular weight of the resultant intended lactic acid polymer and the molecular fractions are shown in Table 1.

Reference Examples C2 to 6

Lactic acid polymers of the present invention were obtained in the same manner as in Reference Example C1. The weight-average molecular weight of the lactic acid polymer of higher molecular weight used, the weight-average molecular weight of the lactic acid polymer after hydrolysis treatment, the weight-average molecular weight of the resultant intended lactic acid polymer and the molecular fractions are shown in Table 1.

TABLE 1

| | | Reference Example C | | | | | |
|---|---|---|---|---|---|---|---|
| | | 1 | 2 | 3 | 4 | 5 | 6 |
| Mw of lactic acid polymer of higher molecular weight | | 40500 | 43600 | 40400 | 43300 | 38600 | 55000 |
| Mw after hydrolysis | | 22200 | 22200 | 22700 | 22200 | 18600 | 27200 |
| Mw of resulted lactic acid polymer | | 22900 | 22200 | 21900 | 22300 | 19400 | 28200 |
| Molecular weight fractions (%) | 1~1000 | 0.03 | 0.07 | 0.00 | 0.01 | 0.08 | 0.04 |
| | 1~3000 | 0.95 | 1.12 | 0.87 | 0.09 | 1.45 | 0.62 |
| | 1~5000 | 3.86 | 4.17 | 3.89 | 3.92 | 4.89 | 2.50 |

As apparent from Table 1, it is known that the lactic acid polymer of the present invention obtained according to the method of the present invention has a fraction of polymer having molecular weights of 5000 or less of about 5% by weight or less, a fraction of polymer having molecular weights of 3000 or less of about 1.5% by weight or less and a fraction of polymer having molecular weights of 1000 or less of about 0.1% by weight or less.

Example A

Composition Containing Hydroxynaphthoic Acid

Example A1

A solution prepared by dissolving 144.4 g of a DL-lactic acid polymer (weight-average molecular weight: 22500, carboxyl group amount by a labeling quantification method: 66.7 µmol/g) into 111.7 g of dichloromethane, and 147.2 g of a solution prepared by dissolving 7.5 g of 3-hydroxy-2-naphthoic acid into 175.1 g of dichloromethane and 13.5 g of ethanol, were mixed and controlled to 28.7° C. 274.4 g of a portion of this organic solvent solution was weighed, and mixed with an aqueous solution obtained by dissolving 24.89 g of an acetate of peptide A into 23.47 g of distilled water and heating to 54.5° C., and the mixture was stirred for 5 minutes for rough emulsification, then, emulsified by using a homogenizer under conditions of 10046 rpm for 5 minutes, to form a W/O emulsion. Then, this W/O emulsion was cooled to 15.0° C., then, poured into 25 L of a 0.1% (w/w) polyvinyl alcohol (EG-40, manufactured by Nippon Synthetic Chemical Industry Co., Ltd.) aqueous solution controlled previously to 15.0° C. over 3 minutes and 26 seconds, and stirred at 7000 rpm by using HOMOMIC LINE FLOW (manufactured by Tokushu Kika K.K.) to give a W/O/W emulsion. This W/O/W emulsion was temperature-controlled for 30 minutes at about 15° C., then, stirred for 2 hours and minutes without temperature-controlling to evaporate dichloromethane and ethanol or scatter dichloromethane and ethanol into the outer water phase, causing solidification of the oil phase, then, sieved through a sieve having an opening of 75 µm, then, microcapsules were continuously precipitated at 2000 rpm using a centrifugal separator (H-600S, manufactured by Kokusanenshinki) and the precipitated microcapsules were collected. The collected microcapsules were re-dispersed in a small amount of distilled water, and sieved through a sieve having an opening of 90 µm, then, to this was added 15.4 g of mannitol causing dissolution, then, the solution was freeze-dried to give a powder. The recovered weight of the microcapsule powder was 101.6 g, meaning a recovery of 72.7%, and the peptide A content was 15.88%, and 3-hydroxy-2-naphthoic acid content was 2.82%.

Experiment Example A1

About 45 mg of the microcapsules described in Example A1 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 2.

TABLE 2

| Remaining ratio: peptide A | |
|---|---|
| One day after | 92.1% |
| One week after | 87.4% |
| Two weeks after | 78.1% |
| Four weeks after | 64.8% |
| Eight weeks after | 51.5% |
| Twelve weeks after | 38.7% |
| Sixteen weeks after | 25.6% |
| Twenty weeks after | 11.8% |
| Twenty six weeks after | 2.0% |

As apparent from Table 2, it is known that the microcapsule of Example A1 produced by adding 3-hydroxy-2-naphthoic acid can contain a physiologically active substance in high content even if produced at a scale of about 125 g, and simultaneously has the effect of suppressing extremely efficiently the initial excess release of a physiologically active substance. Further, this microcapsule allows release of a physiologically active substance at a constant speed for a very long period of time.

Example B

Composition Containing No Hydroxynaphthoic Acid

Example B1

4.00 g of a DL-lactic acid polymer (weight-average molecular weight: 18300, carboxyl group amount by a labeling quantification method: 86 µmol/g) was dissolved in 6.77 g of dichloromethane to give a solution. All of this organic solvent solution was weighed, and mixed with an aqueous solution obtained by dissolving 1.04 g of an acetate of peptide A into 0.92 g of distilled water and heated to 60° C., and the mixture was emulsified by using a homogenizer under conditions of 25000 rpm and 20 seconds, to form a W/O emulsion. Then, this W/O emulsion was poured into 1 L of a 0.1% (w/w) polyvinyl alcohol (EG-40, manufactured by Nippon Synthetic Chemical Industry Co., Ltd.) aqueous solution controlled previously to 18.0° C. over 20 seconds, and stirred at 7000 rpm by using a homomixer to give a W/O/W emulsion. This W/O/W emulsion was stirred at room temperature for 3 hours to evaporate dichloromethane and ethanol or scatter dichloromethane and ethanol into the outer water phase, causing solidification of the oil phase, then, sieved through a sieve having an opening of 75 µm, then, washed with purified water and the microcapsules were precipitated using a centrifugal separator (05PR-22: HITACHI) at 2500 rpm over 5 minutes and the precipitated microcapsules were collected. The collected microcapsules were re-dispersed in a small amount of distilled water, and to this was added 0.50 g of mannitol causing dissolution, then, the solution was freeze-dried to give a powder. The recovered weight of the microcapsule powder was 2.12 g, meaning a recovery of 38.2%, and the peptide A content was 12.98%.

Experiment Example B2

4.40 g of a DL-lactic acid polymer (weight-average molecular weight: 18300, carboxyl group amount by a labeling quantification method: 86 µmol/g) was dissolved in 7.40 g of dichloromethane to give a solution. All of this organic solvent solution was weighed, and mixed with an aqueous solution obtained by dissolving 0.60 g of an acetate of peptide A into 0.552 g of distilled water and heated to 60° C., and the mixture was emulsified by using a homogenizer under conditions of 25000 rpm and 20 seconds, to form a W/O emulsion. Then, this W/O emulsion was poured into 1 L of a 0.1% (w/w) polyvinyl alcohol (EG-40, manufactured by Nippon Synthetic Chemical Industry Co., Ltd.) aqueous solution controlled previously to 18.0° C. over 20 seconds, and stirred at 7000 rpm by using a homomixer to give a W/O/W emulsion. This W/O/W emulsion was stirred at room temperature for 3 hours to evaporate dichloromethane and ethanol or scatter dichloromethane and ethanol into the outer water phase, causing solidification of the oil phase, then, sieved through a sieve having an opening of 75 then, washed with purified water and the microcapsules were precipitated using a centrifugal separator (05PR-22: HITACHI) at 2500 rpm over 5 minutes and the precipitated microcapsules were collected. The collected microcapsules were re-dispersed in a small amount of distilled water, and to this was added 0.50 g of mannitol causing dissolution, then, the solution was freeze-dried, then dried in vacuo at about 50° C. for 48 hours to give a powder. The recovered weight of the microcapsule powder was 3.04 g, meaning a recovery of 55.3%, and the peptide A content was 9.210.

Experiment Example B3

8.10 g of a DL-lactic acid polymer (weight-average molecular weight: 21900, carboxyl group amount by a labeling quantification method: 75.8 μmol/g) was dissolved in 14.15 g of dichloromethane to give a solution. All of this organic solvent solution was weighed, and mixed with an aqueous solution obtained by dissolving 0.93 g of an acetate of peptide A into 0.95 g of distilled water and heated to 60° C., and the mixture was emulsified by using a homogenizer under conditions of 25000 rpm and 20 seconds, to form a W/O emulsion. Then, this W/O emulsion was poured into 1 L of a 0.1% (w/w) polyvinyl alcohol (EG-40, manufactured by Nippon Synthetic Chemical Industry Co., Ltd.) aqueous solution controlled previously to 18.0° C. over 20 seconds, and stirred at 7000 rpm by using a homomixer to give a W/O/W emulsion. This W/O/W emulsion was stirred at room temperature for 3 hours to evaporate dichloromethane and ethanol or scatter dichloromethane and ethanol into the outer water phase, causing solidification of the oil phase, then, sieved through a sieve having an opening of 75 μm, then, washed with purified water and the microcapsules were precipitated using a centrifugal separator (05PR-22: HITACHI) at 2500 rpm over 5 minutes and the precipitated microcapsules were collected. The collected microcapsules were re-dispersed in a small amount of distilled water, and to this was added 1.00 g of mannitol causing dissolution, then, the solution was freeze-dried, then dried in vacuo at about 50° C. for 30 hours to give a powder. The recovered weight of the microcapsule powder was 5.44 g, meaning a recovery of 54.17%, and the peptide A content was 8.03%.

Experiment Example B4

205.5 g of a DL-lactic acid polymer (weight-average molecular weight: 21400, carboxyl group amount by a labeling quantification method: 76.1 μmol/g) was dissolved in 354.3 g of dichloromethane to give a solution which was filtered under pressure through a 0.2 μm filter (EMFLOW, DFA4201FRP), and the temperature was controlled to 28.8° C. 380.4 g of this organic solvent solution was weighed, and mixed with an aqueous solution obtained by dissolving 16.11 g of an acetate of peptide A into 16.22 g of distilled water and heated to 55.4° C., and the mixture was coarsely emulsified by stirring for 1 minute, then, emulsified by using a minimixer under conditions of 10150 rpm and 2 minutes, to form a W/O emulsion. Then, this W/O emulsion was cooled to 18° C., then, poured into 25 L of a 0.10 (w/w) polyvinyl alcohol (EG-40, manufactured by Nippon Synthetic Chemical Industry Co., Ltd.) aqueous solution controlled previously to 18.7° C. over 3 minutes and 10 seconds, and stirred at 7001 rpm by using HOMOMIC LINE FLOW (manufactured by Tokushu Kika K.K.) to give a W/O/W emulsion. This W/O/W emulsion was temperature-controlled for 30 minutes at about 18.5° C., then, stirred for 2 hours and 30 minutes without temperature-controlling to evaporate dichloromethane and ethanol or scatter dichloromethane and ethanol into the outer water phase, causing solidification of the oil phase, then, sieved through a sieve having an opening of 75 μm, then, microcapsules were continuously precipitated at 2000 rpm using a centrifugal separator (H-600S, domestic centrifugal separator) and the precipitated microcapsules were collected. The collected microcapsules were re-dispersed in a small amount of distilled water, and sieved through a sieve having an opening of 90 μm, then, to this was added 18.85 g of mannitol causing dissolution, then, the solution was freeze-dried to give a powder. The recovered weight of the microcapsule powder was 117.6 g, meaning a recovery of 68.54%, and the peptide A content was 7.76%.

Experiment Example B5

4.80 g of a DL-lactic acid polymer (weight-average molecular weight: 28800, carboxyl group amount by a labeling quantification method: 78.1 μmol/g) was dissolved in 7.8 g of dichloromethane to give a solution. All of this organic solvent solution was weighed, and mixed with an aqueous solution obtained by dissolving 1.20 g of an acetate of peptide A into 1.2 g of distilled water, and the mixture was emulsified by using a homogenizer under conditions of 25000 rpm and 20 seconds, to form a W/O emulsion. Then, this W/O emulsion was poured into 1.2 L of a 0.1% (w/w) polyvinyl alcohol (EG-40, manufactured by Nippon Synthetic Chemical Industry Co., Ltd.) aqueous solution controlled previously to 15.0° C. over 20 seconds, and stirred at 7000 rpm by using a homomixer to give a W/O/W emulsion. This W/O/W emulsion was stirred at room temperature for 3 hours to evaporate dichloromethane and ethanol or scatter dichloromethane and ethanol into the outer water phase, causing solidification of the oil phase, then, sieved through a sieve having an opening of 75 μm, then, washed with purified water and the microcapsules were precipitated using a centrifugal separator (05PR-22: HITACHI) at 2200 rpm over 5 minutes and the precipitated microcapsules were collected. The collected microcapsules were re-dispersed in a small amount of distilled water, and to this was added 0.30 g of mannitol causing dissolution, then, the solution was freeze-dried to give a powder. The recovered weight of the microcapsule powder was 3.42 g, meaning a recovery of 53.56%, and the peptide A content was 11.08%.

Experiment Example B1

About 69 mg of the microcapsules described in Example B1 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in-them was quantified and divided by the initial content to give remaining ratio shown in Table 3.

TABLE 3

| Remaining ratio: peptide A | |
| --- | --- |
| One day after | 89.7% |

As apparent from Table 3, the microcapsule of Example B1 produced by compounding peptide A excessively can contain a physiologically active substance in high content, and simultaneously has the effect of efficiently suppressing the initial excess release of a physiologically active substance. Further, from another lot of the same formulation, this microcapsule achieves release of a physiologically active substance at a constant speed for a very long period of time.

Experiment Example B2

About 73 mg of the microcapsules described in Example B2 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 4.

TABLE 4

| Remaining ratio: peptide A | |
| --- | --- |
| One day after | 95.2% |
| Two weeks after | 86.2% |

As apparent from Table 4, the microcapsule of Example B2 produced by compounding only peptide A can contain a physiologically active substance, suppresses sufficiently the initial release of a physiologically active substance, and releases the drug at approximately a constant speed over a long period of time.

Experiment Example B3

About 112 mg of the microcapsules described in Example B3 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 5.

TABLE 5

| Remaining ratio: peptide A | |
| --- | --- |
| One day after | 87.7% |

As apparent from Table 5, the microcapsule of Example B3 produced by compounding only peptide A can contain a physiologically active substance, suppresses sufficiently the initial release of a physiologically active substance, and releases the drug at approximately a constant speed over a long period of time.

Experiment Example B4

About 116 mg of the microcapsules described in Example B4 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 6.

TABLE 6

| Remaining ratio: peptide A | |
| --- | --- |
| One day after | 84.7% |

As apparent from Table 6, the microcapsule of Example B4 produced by compounding only peptide A can contain a physiologically active substance, suppresses sufficiently the initial release of a physiologically active substance, and releases the drug at approximately a constant speed over a long period of time.

Experiment Example B5

About 48.7 mg of the microcapsules described in Example B5 were dispersed in 0.3 ml of a dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 7.

TABLE 7

| Remaining ratio: peptide A | |
| --- | --- |
| One day after | 83.1% |
| Two weeks after | 73.0% |
| Four weeks after | 65.3% |
| Eight weeks after | 49.1% |
| Twelve weeks after | 37.5% |
| Sixteen weeks after | 25.7% |
| Twenty weeks after | 13.6% |
| Twenty six weeks after | 2.4% |
| Twenty eight weeks after | 1.4% |

As apparent from Table 7, the microcapsule of Example B5 produced by compounding only peptide A can contain a physiologically active substance, and suitably suppressed the initial excess release of a physiologically active substance. Further, this microcapsule achieved release of a physiologically active substance at a constant speed for a very long period of time.

Reference Example C7

A solution prepared by dissolving 206.6 g of a DL-lactic acid polymer (weight-average molecular weight: 21,900) into 354.8 g of dichloromethane was warmed and maintained at approximately 30° C. 381.5 g of a portion of this solution was weighed out, and mixed with an aqueous solution obtained by dissolving 15.8 g of leuproreline acetate into 16.6 g of aqueous glacial acetic acid solution (0.6 g of glacial acetic acid was dissolved into 31.75 g of distilled water) and heating to about 55° C., and then, emulsified by using a minimixer (manufactured by Tokushu Kika K.K.) to form a W/O emulsion (rotation rate: approximately 10,000 rpm). Then, this W/O emulsion was cooled to 18.0° C., poured into 25 L aqueous solution containing 0.1% (w/w) polyvinyl alcohol (EG-40, manufactured by Nippon Synthetic Chemical Industry Co., Ltd.) and 1% mannitol which was controlled previously to about 18.0° C., and then emulsified secondarily by using HOMOMIC LINE FLOW (manufactured by Tokushu Kika K.K.) to form a W/O/W emulsion (rotation rate of turbine: about 7,000 rpm; rotation rate of circulation pump: about 2,000 rpm). This W/O/W emulsion was dried in water for about 3 hours, sieved through a standard sieve having an opening of 75 μm, and then, microspheres were continuously precipitated using a centrifugal separator (H-6005, domestic centrifugal separator) (rotation rate: about 2,000 rpm; flow rate: about 600 ml/min) and the precipitated microspheres were collected. The collected microspheres were re-dispersed in a small amount of distilled water, sieved through a standard sieve having an opening of 90 μm, which was added 18.9 g of mannitol, and lyophilized by using lyophilizer (TRIOMASTER, manufactured by Kyouwa Sinkuu K.K.) to obtain a powder (microsphere powder). The leuproreline acetate content of the microsphere obtained was 8.2% and the recovery was about 75%. A W/O emulsion can be obtained successfully by adding acetic acid, and the dispersibility of microcapsule obtained can be improved by adding mannitol into the outer water phase.

Experiment Example C1

About 110 mg of the microcapsule obtained in Reference Example C7 was dispersed into 0.3 ml of dispersion medium (distilled water containing 0.15 mg of carboxymethylcellulose, 0.3 mg of Polysorbate 80 and 15 mg of mannitol, dissolved), and the dispersion was administered via a 22 G injection needle to 7 week old male SD rat subcutaneously in its back. In a given time after administration, the rat was sacrificed and the microcapsules remaining at the administration point were removed, and peptide A contained in them was quantified and divided by the initial content to give remaining ratio shown in Table 8.

TABLE 8

| Remaining ratio: peptide A | |
| --- | --- |
| One day after | 96.6% |
| Two weeks after | 89.8% |
| Four weeks after | 84.1% |

As apparent from Table 2, the microcapsule of Reference Example C7 produced by adding only peptide A can contain a physiologically active substance with high trap efficiency, and it has good dispersibility and also suppressed the initial excess release of a physiologically active substance. Further, this microcapsule releases the physiologically active substance at a constant speed for a very long period of time.

INDUSTRIAL APPLICABILITY

A sustained-release composition of the present invention can contain a physiologically active substance at high content, suppresses the initial excess release, and achieves a stable release speed over a long period of time.

The invention claimed is:

1. A method of producing a controlled release composition comprising a physiologically active substance or salt thereof and a lactic acid polymer or salt thereof having a weight-average molecular weight of 15000 to 50000 in which the content of polymers having molecular weights of 5000 or less is about 5% by weight or less, comprising removing a solvent from a mixed solution of the physiologically active substance or salt thereof and the lactic acid polymer or salt thereof having a weight-average molecular weight of 15000 to 50000 in which the content of polymers having molecular weights of 5000 or less is about 5% by weight or less, wherein the controlled release composition does not contain hydroxynaphthoic acid or salt thereof.

2. The method according to claim 1, wherein the lactic acid polymer has a content of polymers having molecular weights of 3000 or less is about 1.5% by weight or less.

3. The method according to claim 1, wherein the lactic acid polymer has a content of polymers having molecular weights of 1000 or less is about 0.1% by weight or less.

4. The method according to claim 1, wherein the lactic acid polymer has a weight-average molecular weight of 15000 to 40000.

5. The method according to claim 1, wherein the lactic acid polymer has a weight-average molecular weight of 17000 to 26000.

6. The method according to claim 1, wherein the physiologically active substance is a physiologically active peptide.

7. The method according to claim 6, wherein the physiologically active substance is a LH-RH derivative.

8. The method according to claim 7, wherein the LH-RH derivative is a peptide of the formula:

5-oxo-Pro-His-Trp-Ser-Tyr-Y-Leu-Arg-Pro-Z wherein Y represents DLeu, DAla, DTrp, DSer(tBu), D2Nal or DHis(ImBzl), and wherein Z represents NH—$C_2H_5$ or Gly-$NH_2$, or a salt thereof.

9. The method according to claim 7, wherein the LH-RH derivative or salt thereof is contained in an amount of 3% (w/w) to 24% (w/w) in the controlled release composition.

* * * * *